United States Patent
Schultz

(10) Patent No.: US 10,415,094 B2
(45) Date of Patent: *Sep. 17, 2019

(54) RISK STRATIFICATION METHOD FOR A PATIENT HAVING A POLYMORPHISM

(71) Applicant: HelicalHelp LLC, Scottsdale, AZ (US)

(72) Inventor: Brent Schultz, Scottsdale, AZ (US)

( * ) Notice: Subject to any disclaimer, the term of this patent is extended or adjusted under 35 U.S.C. 154(b) by 182 days.

This patent is subject to a terminal disclaimer.

(21) Appl. No.: 15/286,597

(22) Filed: Oct. 6, 2016

(65) Prior Publication Data

US 2018/0100195 A1 Apr. 12, 2018

(51) Int. Cl.
*C12Q 1/68* (2018.01)
*C12P 19/34* (2006.01)
*C12Q 1/6886* (2018.01)

(52) U.S. Cl.
CPC ...... *C12Q 1/6886* (2013.01); *C12Q 2600/112* (2013.01); *C12Q 2600/154* (2013.01); *C12Q 2600/156* (2013.01); *C12Q 2600/158* (2013.01)

(58) Field of Classification Search
CPC ............ C12Q 1/6886; C12Q 2600/112; C12Q 2600/154; C12Q 2600/156; C12Q 2600/158
See application file for complete search history.

(56) References Cited

U.S. PATENT DOCUMENTS

| | | | |
|---|---|---|---|
| 5,972,643 | A | 10/1999 | Lobanenkov et al. |
| 7,037,668 | B2 | 5/2006 | Tsai |
| 7,375,206 | B2 | 5/2008 | Lobanenkov et al. |
| 7,625,759 | B2 | 12/2009 | de Sauvage et al. |
| 7,785,814 | B2 | 8/2010 | Lobanenkov et al. |
| 8,735,079 | B2 | 5/2014 | Bergmann et al. |
| 2002/0034781 | A1 | 3/2002 | Glucksmann |
| 2003/0073107 | A1 | 4/2003 | Jupe et al. |
| 2003/0096262 | A1 | 5/2003 | Li et al. |
| 2003/0118991 | A1 | 6/2003 | Shiloh |
| 2010/0093012 | A1 | 4/2010 | Bergmann et al. |
| 2010/0152136 | A1 | 6/2010 | Shaughnessy, Jr. et al. |
| 2011/0014607 | A1 | 1/2011 | Jirtle et al. |
| 2011/0112186 | A1 | 5/2011 | Link et al. |
| 2011/0147218 | A1 | 6/2011 | Meyer et al. |
| 2011/0294121 | A1 | 12/2011 | Deangelis |
| 2012/0142546 | A1 | 6/2012 | Califano et al. |
| 2012/0237520 | A1 | 9/2012 | Lobanenkov et al. |
| 2012/0238455 | A1 | 9/2012 | Nakamura et al. |
| 2015/0376612 | A1 | 12/2015 | Lee et al. |

FOREIGN PATENT DOCUMENTS

WO 2006082414 A1 8/2006

OTHER PUBLICATIONS

Esteves, L.I.D.C.V. et al, International Journal of Molecular Medicine, 17:397-404 (Year: 2006).*
Kim T.H. et al. Cell 128, 1231-1245, Mar. 23, 2007.*
PstI, from https://www.neb.com/products/r0140-psti, pp. 1-9, printed on Jan. 28, 2019 (Year: 2019).*
Rs10732516 Reference SNP (rs) Report, from https://www.ncbi.nlm.nih.gov/snp/rs10732516, pp. 1-10printed on Jan. 28, 2019 (Year: 2019).*
Schultz B. et al., PLoS ONE 10(10): e0113168. doi:10.1371/journal.pone.0113168, pp. 1-24 (Year: 2015).*
Schultz, B.E., et al. Abstract 202: A Common Polymorphism Within the IGF2 Imprinting Control Region is Associated With Parent of Origin Specific Effects in Infantile Hemangiomas , Plastic and Reconstructive Surgery, Issue: vol. 131(5S) PSRC 2013 Abstract Supplement, May 2013, p. 148 (Year: 2013).*

* cited by examiner

*Primary Examiner* — Stephen T Kapushoc
(74) *Attorney, Agent, or Firm* — Invention To Patent Services; Alex Hobson

(57) ABSTRACT

A risk stratification method for a patient in a disease state and specifically patients presenting a tumor, includes determining if the patient is a homozygote or heterozygote and further determining the allelic expression for the patient, CC, T/C, or C/T. For patients having the cytosine methylated, they have a T|C allelic expression and patients without a methylated cytosine have a C/T allelic expression. A patient with a TT allelic expression is classified as a highest risk patient, a patient with a T|C allelic expression is classified as a second highest risk patient, a patient with a C/T allelic expression is classified as a third highest risk patients and a patient with a CC allelic expression is classified as a lowest risk patient. The risk stratification method may further include identification of an abnormal expression or mutation/function of a gene product produced by CTCF binding site 6.

12 Claims, 15 Drawing Sheets

Specification includes a Sequence Listing.

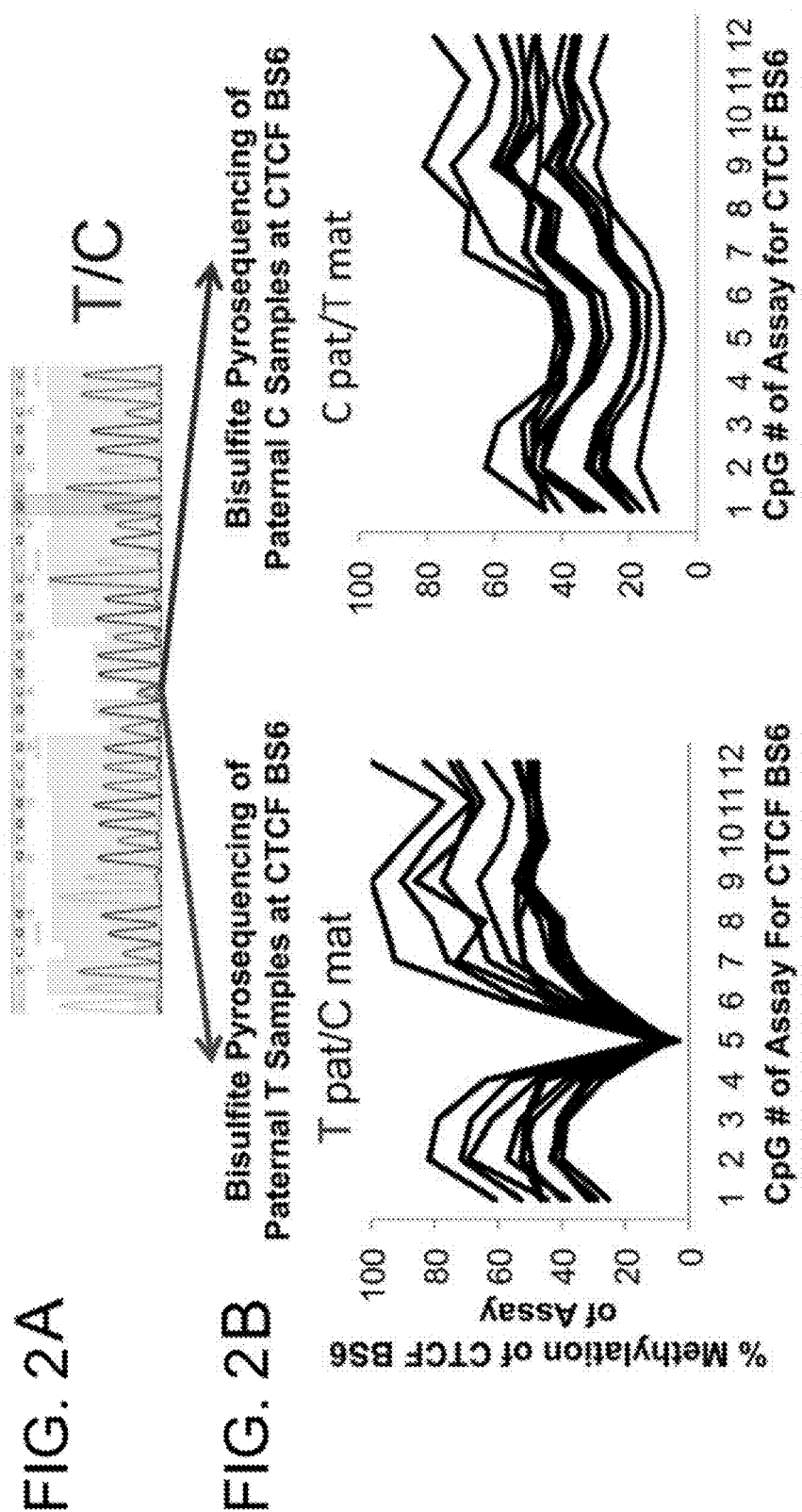

| IH Number | Genotype: Pat/Mat | Clinical Study | Region | Age (days) | First Appeared | Phase | Sex | Oral Steroid | Inj Steroid | Chemo | Laser | Ulceration |
|---|---|---|---|---|---|---|---|---|---|---|---|---|
| bCTCF/B19 CTCF/BORIS qPCR | | | | | | | | | | | | |
| 1 | T/C | Y | L Lower Eyelid | 95 | 1 Week | Prolif | F | | | | | |
| 2 | T/C | Y | Upper lip | 368 | Near Birth | Prolif | F | | | | | |
| 3 | T/C | Y | L Paranasal | 418 | 1 Week | Quiescent | F | | | | + | + |
| 4 | T/T | Y | R Malar | 420 | 1 Week | Quiescent | F | + | | + | + | + |
| 5 | T/T | Y | Lip and Nose | 635 | Near Birth | Quiescent | F | | | | | |
| 6 | T/T | Y | Lip and Nose | 2138 | Near Birth | Invol | M | + | | + | + | + |
| 7 | T/C | Y | L Preauricular | 2304 | Near Birth | Invol | M | | | | | |
| 8 | C/T | Y | L Upper Eyelid | 95 | 3 Weeks | Prolif | F | | | | | |
| 9 | C/A | N | Neck | 165 | near birth | prolif | F | | | | | |
| 10 | C/A | N | Nasal Tip | 334 | near birth | prolif | F | | | | | |
| 11 | C/A | N | Nasal Tip | 365 | near birth | prolif | M | | | | | |
| 12 | C/C | Y | Nasal Tip | 547 | 2 Weeks | Quiescent | F | + | | | + | |
| 13 | C/C | Y | Scalp | 760 | 2 Weeks | Quiescent | F | | | | | |
| 14 | C/T | Y | Nasal Dorsum | 1500 | Near Birth | Invol | F | | | | | |
| Additional CTCF/BORIS qPCR | | | | | | | | | | | | |
| 15 | N/A | N | scalp | 81 | Near Birth | Prolif | M | + | | + | + | |
| 16 | N/A | N | Nasal Tip | 299 | | Prolif | M | | | | + | + |
| 17 | N/A | N | Neck | 380 | | Prolif | F | | | | | |
| 18 | N/A | N | R Cheek | 752 | | Quiescent | M | | | | | |
| 19 | N/A | N | Scalp | 1171 | | Invol | F | | | | | |
| Western and | | | | | | | | | | | | |

FIG. 10A

| IH Number | Genotype Pat/Mat | Clinical Study | Region | Age (days) | First Appeared | Phase | Sex | Oral Steroid | Inj Steroid | Chemo | Laser | Ulceration |
|---|---|---|---|---|---|---|---|---|---|---|---|---|
| IG2119 CT/CT/BOR1 | | | | | | | | | | | | |
| 20 | T/C | Y | Forehead | 104 | 1 Week | Prolif | F | | | | | |
| 21 | T/T | Y | Neck | 210 | 1 week | prolif | F | + | | | | + |
| 22 | C/T | N | Back | 244 | "Near Birth" | Prolif | F | | | | | |
| 23 | T/C | N | Chest Wall | 294 | "Near Birth" | Prolif | F | | | | | |
| 24 | T/T | Y | Forehead | 308 | 2 Weeks | Prolif | F | + | | | | + |
| 25 | C/C | Y | Upper Lip | 367 | 3 Weeks | Quiescent | F | | | | | |
| 26 | T/T | Y | Forehead | 435 | 2 weeks | Quiescent | F | + | | | | + |
| 27 | C/C | Y | Upper Lip | 608 | Near Birth | Quiescent | M | | | | | |
| 28 | T/T | Y | L Pre Auricular | 731 | 2 Weeks | Quiescent | F | | | | | |
| 29 | C/C | N | Back | 987 | 1 Week | Invol | F | | | | | |
| 30 | C/C | Y | Neck | 1600 | Near Birth | Invol | F | | | | | |
| 31 | C/C | Y | R Upper Eyelid | 1772 | Near Birth | Quiescent | F | | | | | |
| 32 | C/C | Y | Nasal Tip | 2023 | "Near Birth" | Quiescent | F | | | | | |
| BNA.019 | | | | | | | | | | | | |
| 33 | C/T | Y | Neck | 21 | 2 Weeks | Prolif | F | | | | | |
| 34 | T/T | Y | L Upper Eyelid | 96 | 3 Weeks | Prolif | F | | | | | |
| 35 | T/C | Y | Forehead | 285 | 1 Week | Prolif | F | | | | | |
| 36 | T/T | Y | Paranasal | 333 | 2 Weeks | Prolif | F | + | | | + | |
| 37 | C/T | Y | Lower Lip | 407 | "Near Birth" | Quiescent | F | | | | | + |
| 38 | C/C | Y | L Cheek | 531 | "Near Birth" | Quiescent | F | | | | | |
| 39 | T/C | Y | Lower Lip | 1146 | 2 Weeks | Quiescent | F | + | | | | |
| 40 | C/C | Y | Forehead | 1263 | "Near Birth" | Prolif | F | | | | | |
| Excluded | | | | | | | | | | | | |
| 41 | N/A | N | R Cheek | 286 | | | | | | | | |
| 42 | N/A | N | Nasal | 2240 | | | | | | | | |

FIG. 10B

| Reason for Excision | Western | CTCF | BORIS | IGF2 | H19 | % H19 Meth Pyro | % H19 Meth Southern | % H19 Meth Blood Pyro |
|---|---|---|---|---|---|---|---|---|
| Threatened Visual Axis | | 0.65 | 0.20 | 1.61 | 1.58 | | | |
| Cosmesis | Y | 8.00 | 5.20 | 1.20 | N/A | 32.2 | | |
| Cosmesis | Y | 3.65 | 13.34 | 4.35 | 4.59 | | | |
| Ulceration | Y | 0.87 | 6.76 | 3.25 | 2.22 | 29.2 | 26 | |
| Ulceration | Y | 2.21 | 9.89 | 4.75 | 2.65 | | | |
| Ulceration | Y | 11.55 | 2.91 | 0.38 | 3.65 | 14 | 14 | |
| Cosmesis | Y | 0.60 | 0.40 | 0.60 | 0.20 | 29 | 35 | |
| Threatened Visual Axis | | 0.89 | 0.55 | 1.99 | 2.28 | 26.5 | 25.8 | |
| Parental Preference | | 0.70 | 8.30 | 1.30 | 1.60 | | | |
| Cosmesis | | 1.10 | 1.40 | 1.40 | 2.60 | | | |
| Cosmesis | Y | 1.00 | 1.30 | 2.20 | 2.00 | | | |
| Cosmesis | Y | 2.14 | 2.39 | 2.54 | 2.60 | 27.5 | 35 | |
| Parental Preference | Y | 1.08 | 2.60 | 3.99 | 2.89 | | | |
| Cosmesis | Y | 3.00 | 2.09 | 1.00 | 2.62 | 21 | | |
| Ulceration | | 0.73 | 0.07 | | | | | |
| Ulceration | | 1.86 | 1.28 | | | | | |
| Parental Preference | | 0.70 | 0.88 | | | | | |
| Cosmesis | | 0.85 | 0.91 | | | | | |
| Cosmesis | | 2.13 | 0.91 | | | | | |

FIG. 10C

| Reason for Excision | Western | CTCF | BORIS | IGF2 | H19 | % H19 Meth Pyro | % H19 Meth Southern | % H19 Meth Blood Pyro |
|---|---|---|---|---|---|---|---|---|
| Parental Preference | | | | | | | | |
| Ulceration | Y | | | | | 32.4 | 34 | 63.9 |
| Cosmesis | Y | | | | | | | |
| Cosmesis | Y | | | | | 35.7 | 27.5 | 61.4 |
| Ulceration | Y | | | | | 27.1 | 26 | 54.2 |
| Cosmesis | Y | | | | | 34.8 | 21 | 57.4 |
| Ulceration | Y | | | | | | 29.5 | 55.6 |
| Cosmesis | Y | | | | | 26.7 | 23 | |
| Cosmesis | Y | | | | | | | |
| Cosmesis | Y | | | | | 25.8 | 23 | 61.4 |
| Cosmesis | Y | | | | | 23.2 | 19 | |
| Cosmesis | Y | | | | | 21.6 | 22 | 64.8 |
| Cosmesis | Y | | | | | 23.1 | 25 | 53.4 |
| Rapid Growth | | | | | | | | |
| Threatened Visual Axis | | | | | | | | |
| Cosmesis | | | | | | 17.7 | 28 | 55.1 |
| Ulceration | | | | | | 28.8 | | |
| Cosmesis | | | | | | 17.8 | 27 | 56.2 |
| Cosmesis | | | | | | 33.9 | 30.5 | 52.9 |
| Cosmesis | | | | | | 24.4 | | |
| Cosmesis | | | | | | | | |
| Not Clut 1 Positive | | | | | | | | |
| Prior Resection of Same Lesion | | | | | | | | |

FIG. 10D

| Genotype: Pat/Mat | Region | Age (days) | First Appear | Size (cm) | Phase | Sex | Oral Steroid | Inj Steroid | Chemo | Laser | Ulceration | Ulcerated After Laser |
|---|---|---|---|---|---|---|---|---|---|---|---|---|
| T/T | R Malar | 180 | 2 Weeks | 4 | Prolif | F | + | | | + | + | |
| T/T | Neck | 205 | Near Birth | 6 | Prolif | F | + | | | | + | |
| T/T | Neck | 435 | Near Birth | 7 | Quiescent | F | + | | | | + | |
| T/T | Forehead | 175 | 2 Weeks | 4 | Quiescent | F | + | | | | | |
| T/T | R Malar | 420 | 1 Week | 10 | Prolif | F | + | | + | + | + | |
| T/T | Lip and Nose | 429 | Near Birth | 9 | Quiescent | F | + | | | + | + | + |
| T/T | R Pre-Auricular | 358 | 2 Weeks | 5 | Quiescent | F | | | | | | |
| T/T | L Upper Eyelid | 95 | 3 Weeks | 2 | Prolif | F | | | | | | |
| T/T | Lip and Nose | 180 | Near Birth | 3.5 | prolif | M | + | + | | + | + | + |
| C/T | Nasal Dorsum | 1000 | Near Birth | 3 | Quiescent | F | | + | | | | |
| C/T | L Upper Eyelid | 95 | 2 Weeks | 1.7 | Prolif | F | | + | | | | |
| C/T | Lower Lip | 407 | Near Birth | 1.5 | Quiescent | F | | | | | | |
| C/T | Neck | 21 | 2 Weeks | 1 | Prolif | F | | | | | | |
| T/C | Lower Lip | 500 | 2 Weeks | 3 | Quiescent | F | | | | + | | |
| T/C | Upper Lip | 368 | Near Birth | 2 | Quiescent | F | | | | | | |
| T/C | L Lower Eyelid | 95 | 1 Week | 2 | Prolif | F | | | | | | |
| T/C | L Preauricular | 1050 | Near Birth | 6 | Quiescent | M | | | | | | |
| T/C | L Paranasal | 120 | 1 Week | 2.5 | Quiescent | F | | + | | | | |
| T/C | Forehead | 60 | 1 Week | 1 | Prolif | F | | | | | | |
| T/C | Forehead | 68 | 1 Week | 2 | Prolif | F | | | | | | |
| CC | Scalp | 685 | 2 Weeks | 3 | Quiescent | F | | | | | | |
| CC | Forehead | 365 | Near Birth | 2 | Prolif | F | | | | | | |
| CC | Upper Lip | 365 | Near Birth | 1.5 | Quiescent | M | | | | | | |
| CC | Nasal Tip | 720 | Near Birth | 2 | Quiescent | F | | | | | | |
| CC | Upper Lip | 123 | 3 Weeks | 2.5 | Prolif | F | | + | | | | |
| CC | Nasal Tip | 250 | 2 Weeks | 2 | Quiescent | F | + | + | | + | | |
| CC | L Cheek | 531 | Near Birth | 3 | Quiescent | F | | | | | | |
| CC | Neck | 270 | Near Birth | 4 | Quiescent | F | | | | | | |
| CC | R Upper Eyelid | 1000 | Near Birth | 2 | Quiescent | F | | | | | | |

FIG. 11

CLINICAL TABLE OF ULCERATION BY TT AND NON-TT GENOTYPE

|        | Ulcerated | Not Ulcerated |
|--------|-----------|---------------|
| TT     | 6         | 3             |
| Non TT | 0         | 20            |

Sensitivity = 100%
Specificity = 86.96%
Positive Predictive Value = 66.67%
Negative Predictive Value = 100%

Retrospectively collected results with associated descriptive statistics: TT Lesions have a significantly higher associated odds ratio for ulceration. This proposed clinical test may be most useful in ruling out the chance of ulceration early in the disease course as sensitivity and negative predictive value are high. A larger prospective study is warranted.

Odds Ratio = 76.1
95% CI = 3.4-1676
P = .006

FIG. 12

SEQUENCE LISTING

<160> NUMBER OF SEQ ID NOS: 2

<210> SEQ ID NO 1
<211> LENGTH: 216
<212> TYPE: DNA
<213> ORGANISM: Homo sapiens
<220> FEATURE:
<221> NAME/KEY: misc_feature
<223> OTHER INFORMATION: Polymorphism in CTCF Binding Site 6 in H19
      differential methylated region

<400> SEQUENCE: 1
tgggtatttc tggaggcttc tccttcggtc tcaccgcctg gatggcacgg aattggttgt    60
agttgtggaa tcggaagtgg ccgcgcggcg gcagtgcagg ctcacacatc acagcccgag   120
cccgccccaa ctggggttcg cccgtggaaa cgtcccgggt cacccaagcc acgcgtcgca   180
gggttcacgg gggtcatctg ggaataggac actcat                             216

<210> SEQ ID NO 2
<211> LENGTH: 216
<212> TYPE: DNA
<213> ORGANISM: Homo sapiens
<220> FEATURE:
<221> NAME/KEY: misc_feature
<223> OTHER INFORMATION: Polymorphism CTCF Binding Site 6 in H19
      differential methylated region

<400> SEQUENCE: 2
tgggtatttc tggaggcttc tccttcggtc tcaccgcctg gatggcacgg aattggttgt    60
agttgtggaa tcggaagtgg ccgcgcggtg gcagtgcagg ctcacacatc acagcccgag   120
cccgccccaa ctggggttcg cccgtggaaa cgtcccgggt cacccaagcc acgcgtcgca   180
gggttcacgg gggtcatctg ggaataggac actcat                             216

RISK STRATIFICATION METHOD FOR A PATIENT HAVING A POLYMORPHISM

BACKGROUND OF THE INVENTION

Field of the Invention

The invention is directed to a risk stratification method for a patient in a disease state and particularly to a patient having a polymorphism and a tumor, such as a hemangioma.

Background

Infantile hemangioma (IH) is the most common tumor of the pediatric age group, affecting up to 4% of newborns ranging from inconsequential blemishes, to highly aggressive tumors. Following well defined growth phases (proliferative, plateau involutional) IH usually regress into a fibrofatty residuum. Despite the high prevalence of IH. little is known regarding the pathogenesis of disease.

Infantile hemangioma (IH) is the most common tumor of the pediatric age group, affecting up to 4% of newborns with nearly 60% localized to the head and neck. These vascular lesions range from inconsequential blemishes to highly aggressive tumors that can cause eye obstructions or blindness, blockage of airways, facial deformations and ulcerations. During the first year, hemangiomas demonstrate both histology and behavior that are also commonly noted in malignancy: immature vascular channels, high mitotic indices, and strong positivity for proliferative markers such as Ki-67.

Despite these ominous beginnings, IH remain benign. The growth velocity slowly reverses leading to a "quiescent or plateau" phase of non-growth (1-2 years) and then transitions into a regressive or "involuting" phase by replacing the once proliferative endothelium with a fibrofatty residuum (2-10 years). However, these growth phases are a matter of clinical judgment alone and the exact timing of each varies considerably among studies. Despite its prevalence, little is known regarding the pathogenesis of disease. Insulin Like Growth Factor 2 (IGF2) has been implicated as an important player in driving the growth of these lesions. IGF2 decreases over six fold from proliferative to involuting IH samples. Furthermore. Beckwith-Wiedmann Syndrome (BWS), where hemangiomas are considered a supportive finding of the diagnosis, is associated with duplications or a loss of imprinting of the IGF2/H19 locus that leads to IGF2 overproduction. Moreover, explant hemangioma cultures grow strongly in response to exogenous IGF2.

IGF2 is an imprinted gene that is usually only expressed from the paternal copy. Commonly, DNA methylation of cytosines preceding guanines (CpG's) reinforce DNA imprinting. These so called epigenetic marks in part determine and are determined by the array of DNA binding proteins capable of interacting with specific chromatin structures. The end result of this process is diploid DNA that is potentially identical in sequence but chemically, transcriptionally and architecturally distinct in a parent of origin specific manner. This leads to activation of one given parental allele and reciprocal silencing of another. The IGF2/H19 region of chromosome 11p15.5 serves as a model for the production of multiple imprinted transcripts.

SUMMARY OF THE INVENTION

The invention is directed to a risk stratification method for a patient in a disease state and particularly to a patient having a polymorphism and a tumor, such as a hemangioma.

Brother of the regulator of imprinted sites or BORIS, also known as transcriptional regulator transcriptional repressor CTCFL, is a protein that in humans is encoded by the CTCFL gene.

With respect to infantile hemangiomas, a reported six fold decrease in IGF2 expression (correlating with transformation of proliferative to involuted lesions) prompted a study of the IGF-2 axis further. As described herein, it has been discovered that IGF2 expression in IH is strongly related to the expression of a cancer testes and suspected oncogene BORIS (paralog of CTCF), placing IH in the unique category of being the first known benign BORIS positive tumor. IGF2 expression was strongly and positively related to BORIS transcript expression. Furthermore, a stronger association was made when comparing BORIS levels against the expression of CTCF via either a percentage or difference between the two, or a rate of increase of % CTCF. A patient with a reducing rate of % CTCF may be a higher risk patient, as this may indicate a more aggressive tumor, as described herein. A common C/T polymorphism at CTCF BS6 appeared to modify the correlation between CTCF/BORIS and IGF2 expression in a parent of origin specific manner. Moreover, these effects may have phenotypic consequences as tumor growth also correlates with the genotype at CTCF BS6. This may provide a framework for explaining the clinical variability seen in IH and suggests new insights regarding CTCF and BORIS related functionality in both normal and malignant states.

Investigations into the differential regulation and potential role of IGF2 as it pertains to IH, as well as the expression of CTCF, a known chromatin insulator element for IGF2 and its antagonist, BORIS (also known as CTCFL—for CTCF like) at both the transcript and protein levels are described herein. The nearby imprinted and maternally expressed H19 gene, which shares enhancers with IGF2, was also quantified. These results were then correlated with methylation analysis of key regulatory regions in the IGF2 and H19 locus. This analysis suggests that a common polymorphism within CTCF Binding Site Six, the critical imprinting control region of H19/IGF2, may have both cellular and phenotypic consequences in a parent of origin specific manner. These findings may serve as a predictor of clinical behavior of IH and may enable risk stratification for patients having a tumor, and specifically IH.

In an exemplary embodiment, a risk stratification method for a patient in a disease state is accomplished by first determining whether said patient is a homozygote patient or a heterozygote patient with respect to CTCF binding site 6. When the patient is a homozygote patient it is then determined if the patient has a Thymine/Thymine, (TT) allelic expression or a Cytosine/Cytosine (CC) allelic expression for said CTCF binding site 6. When the patient is a heterozygote, it is then determined whether the cytosine is methylated; whereby when the cytosine is not methylated the patient has a Thymine/Cytosine, (TC) allelic expression for said CTCF binding site 6; and whereby when the cytosine is methylated the patient has a Cytosine/Thymine (CT) allelic expression for said CTCF binding site 6. A patient with a TC allelic expression has a maternal cytosine and a patient with a CT allelic expression has a paternal cytosine. Risk stratifying can then be determined based on the patient's allelic expression for CTCF binding site 6, wherein the patient with a TT allelic expression is classified as a highest risk patient, the patient with a TC allelic expression is classified as a second highest risk patient, the patient with a CT allelic expression is classified as a third highest risk patient and the patient with a CC allelic expression is classified as a lowest risk patient. Furthermore, unique to the disease of vascular tumors in general and infantile hemangioma specifically is the risk of ulceration. A painful condition where the epithelium of the lesion degrades, creating an open wound prone to bleeding. The TT allelic expression is classified at the highest risk for ulceration.

A highest risk patient having an IH may be prone to a rapidly growing tumor, ulceration of the tumor, facial deformations, eye obstructions, blockage of airways or any combination of these conditions. A second highest risk patient having IH may be prone to moderately to rapidly growing tumors, facial deformations, eye obstructions, blockage or airways or any combination of these conditions. A third highest risk patient having IH may have a slow to moderately growing tumor, facial blemishes. A lowest risk patient having IH may have a slow growing tumor, facial blemishes.

Any suitable method may be used to for determining for a heterozygote patient whether the cytosine is methylated including, bisulfite conversion and quantitative methylation sensitive pyrosequencing or directly sequencing parental DNA, for example.

A risk stratification method, as described herein, may be initiated for a patient in a diseased state, wherein the patient is in a diseased state by identification of a patient tumor. A patient may be considered to be in a diseased state when the identified tumor is an infantile hemangioma, or any other tumor such as a cancerous tumor including, but not limited to, breast cancer, ovarian cancer, testicular cancer, liver cancer, lung cancer, brain cancer, skin cancer, esophageal cancer, throat cancer, bladder cancer, cervical cancer, colorectal cancer, kidney cancer, leukemia, melanoma, non-Hodgkin lymphoma, ovarian cancer, pancreatic cancer, prostate cancer, skin cancer, thyroid cancer, uterine cancer and any other cancer.

The risk stratification as described herein, may further comprise the step of identification of an abnormal expression or mutation/function of a gene regulated by CTCF binding site 6. The abnormal expression or mutation/function of a gene product regulated by CTCF binding site 6 may be IGF2, H19, H19 antisense, IGF2 antisense, a micro ma within the gene locus, or the gene product may be an isoform.

The risk stratification as described herein, may further comprise the step of identification of an abnormal expression or mutation/function of a binding gene product that binds to the CTCF binding site 6. The abnormal expression or mutation/function of a binding gene product that binds to the CTCF binding site 6 may be CTCF, BORIS or a binding isoform.

The risk stratification as described herein, may further comprise the step of identification of an abnormal expression or mutation/function of a binding partner of CTCF or BORIS.

In an exemplary embodiment, a risk stratification method further comprising the steps of determining an expression level of BORIS and an expression level of CTCF with respect to CTCF binding site 6, and then determining a percentage of CTCF transcript, such as the percentage of CTCF with respect to the total of CTCF and BORIS. In an alternative embodiment, a difference in the amount of CTCF to the amount of BORIS may be used. A risk stratification method may take into account the allelic expression, as described herein, and may further take into account the % CTCF, wherein, when the % CTCF is less than 20%, the patient is classified as a highest % CTCF risk patient, wherein when the % CTCF is less than 50% but greater than 20%, the patient is classified as a second highest % CTCF risk patient, wherein when the % CTCF is less than 80% but greater than 50% the patient is classified as a third highest % CTCF risk patient and wherein when the % CTCF ratio is less than 100% or less and greater than 80% the patient is classified as a lowest % CTCF risk patient. Furthermore, the risk stratification method may include the rate of reduction of % CTCF, wherein a rapid drop in % CTCF may indicated a higher risk of an aggressive tumor, or a tumor that grows quickly.

In an exemplary embodiment, a risk stratification method further comprising the steps of determining an expression level of BORIS and an expression level of CTCF with respect to CTCF binding site 6, and then determining a CTCF-BORIS difference which is a difference in the expression level of CTCF to the expression level of BORIS. The patient may then be risk stratified according to said CTCF-BORIS difference wherein, when the CTCF-BORIS difference is less than zero, the patient is classified as a highest CTCF-BORIS risk patient; and when the CTCF-BORIS difference is greater than zero, the patient is classified as a lowest CTCF-BORIS risk patient.

In an exemplary embodiment, the risk stratification method as described herein, may be used to predict a response of medication to the tumor. For example, a patient with a TT allelic expression and classified as a highest risk patient may have a predicted medication response that is most effective, a patient with a TC allelic expression and classified as a second highest risk patient may have a predicted medication response that is second most effective, a patient with a CT allelic expression and classified as a third highest risk patient may have a predicted medication response that is third most effective and a patient with a CC allelic expression and classified as a lowest risk patient may have a predicted medication response that is least effective. Patients classified as the highest risk patients may have the most effective response to medication whereas patients classified as the lowest risk patients may have the least effective response to medication. Medication may be beta blockers, cortical steroids, alpha interferon, and/or IGF2 receptor blockers. Preferred medications are beta blockers and cortical steroid. A most effective response or highly effective response to medication includes slowing of the growth of the tumor, reduction in size of the tumor without rebound or relapse, closure of ulceration or healing or ulceration. A second most effective response to medication includes reduction in size of the tumor without rebound or relapse. T third most effective response to medication includes reduction in size of the tumor without rebound or relapse. A least effective response to medication includes reduction in size of the tumor, or no reduction in size of the tumor.

The medication response prediction method may further comprise the step of determining the disease state of said patient by identification of an abnormal expression or mutation/function of a gene product produced by CTCF binding site 6. The abnormal expression or mutation/function of a gene product regulated by CTCF binding site 6 may be IGF2, H19, H19 antisense, IGF2 antisense, a micro ma within the gene locus, or the gene product may be an isoform.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 2A shows a diagram representing the genotyping via direct sequencing of blood samples.

FIG. 2B shows a chart of bisulfite conversion and quantitative methylation sensitive pyrosequencing.

FIGS. 3A and 3B show a chart of IGF2 transcription by clinical stage wherein FIG. 3A shows IGF2 Transcript and FIG. 3B shows % CTCF.

FIGS. 8A and 88B show a graph of the parent of origin, paternal and maternal respectively, specific effects of CTCF BS6 on IGF2 and H19 transcription.

FIGS. 10A to 10D show portions of Master Table.

FIG. 11 is a table of the summary of clinical data. Retrospectively collected results with associated descriptive information.

FIG. 12 is a table showing incidence of ulceration by TT and non-TT genotype.

DETAILED DESCRIPTION OF THE ILLUSTRATED EMBODIMENTS

Figure 1:
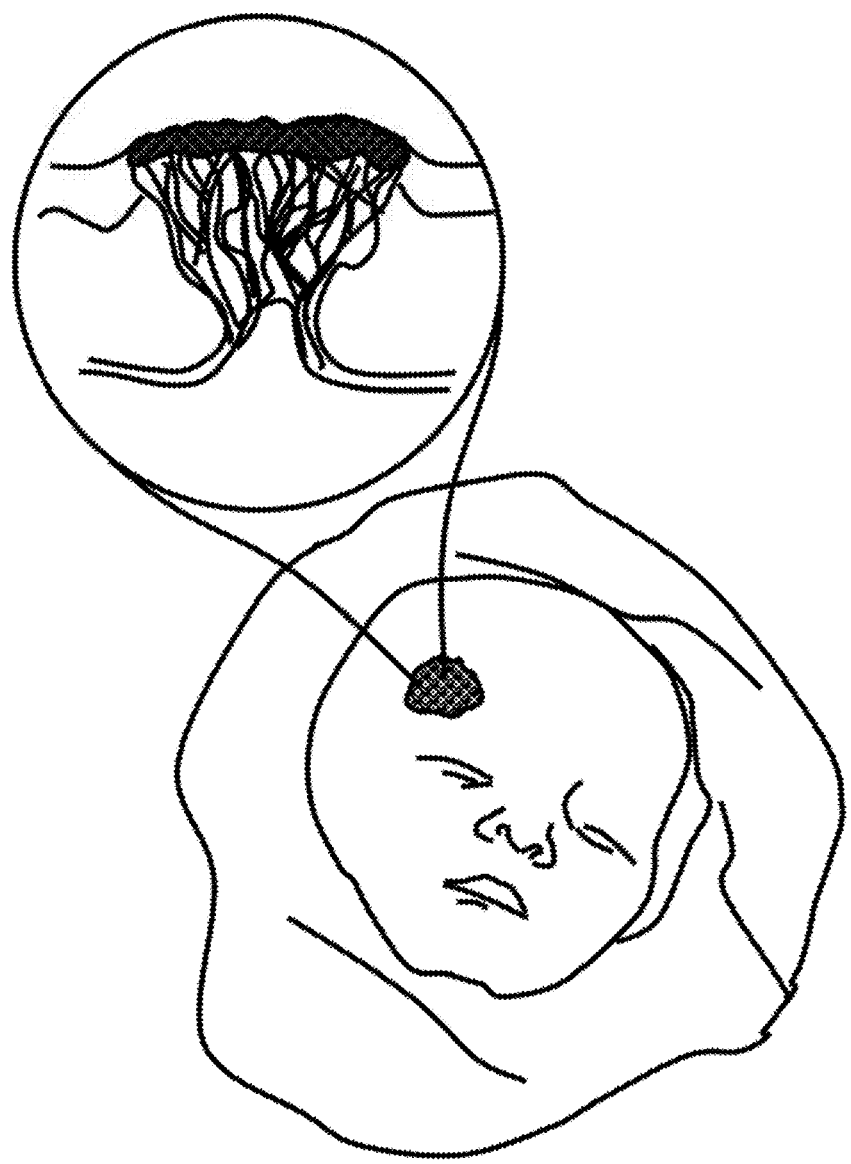
FIG. 1 shows a drawing of an infantile hemangioma.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

This application incorporates by reference in its entirety, the following publication:

Brent Schultz, Xiaopan Yao, Yanhong Deng, Milton Waner, Christopher Spoeck, Laura Tom, John Persing, Deepak Narayan, (2015) A Common Polymorphism Within The IGF2 Imprinting Control Region Is Associated with Parent of Origin Specific Effects in Infantile Hemangiomas, PLOS ONE|DOI:10.1371/journal.pone.0113168

Materials and Methods

This article describes a study that involved analyzing post excisional tissue from surgical candidates. The decision to operate was in no way influenced by the study. Clinical data was gathered retrospectively from this same group. All surgical candidates had clinical measurements available for analysis. All samples and clinical data were collected in accordance with the approved HIC protocol (#0507000430) as reviewed by the Yale University Medical School IRB. This protocol was approved specifically for this study. Written consent was obtained from each patient's legal guardian prior to surgery. All data obtained including clinical measurements were stored in a de-identified format.

Specimen Collection:

Please refer to the FIGS. 10A to 10D, Master Data Table, for details. Those specimens later confirmed to be hemangioma tissue, via Glut-1 positive histology, were considered for this project. Further, only discrete solitary lesions that were not found in the setting of a syndrome were considered. Those patients where prior surgical resections of the lesion were performed were also deemed ineligible. Of note, those lesions previously treated with laser were not excluded, as the effects of laser treatment are relatively superficial. However, during specimen collection, all areas that appeared grossly to be affected by laser treatment were excised before further processing. Briefly, forty-two samples were collected (See FIGS. 10A to 10D for details.) Of these, two samples (#41 and #42), were excluded from all analyses; sample #41 was Glut-1 negative on histology and #42 was subject to prior resections. Nineteen IH samples were selected at random for methylation analysis of the H19 promoter by southern. These 19 samples were also analyzed for methylation specific pyrosequencing of the same region. An additional two samples (numbers 1 and 14) were also subjected to H19 methylation specific pyrosequencing to bolster the number of samples with both H19 methylation and transcriptional data. Regarding transcriptional analysis, nineteen samples were found to have suitably intact RNA for quantitative RT PCR. Specimens for transcriptional analysis were separated into three categories: 1) Proliferative, 2) Quiescent, and 3) Involuting phases. As a lesion's stage is, by definition, clinical, an experienced physician staged the IH at the time of surgery. Data regarding clinical stage was gathered prospectively. The determination of the clinical stage was made by one of three highly experienced surgeons regarding vascular anomalies, using interval growth, patient age and the color/turgor of the lesion at the time of resection as criteria. General characteristics of these categories are as follows: 1) proliferative hemangiomas were generally less than 1.5 years of age with interval growth between the last two clinical visits preceding surgery, no lightening of lesion color was noted. 2) Quiescent hemangiomas: no interval growth between the last two clinic visits preceding surgery, lightening of color also played a factor in these determinations. Involuting hemangiomas: interval regression by measurement between the last two clinic visits preceding surgery, further color changes were often but not always noted, as shown in FIGS. 10A to 10D.

FIGS. 10A to 10D: Master Data Table. All samples are assigned arbitrary numbers for ease of reference. Samples are categorized according to which set of experiments were performed, then by paternal/maternal genotype regarding the IGF2 rtPCR experiment. All sub categories are then sorted by age at resection. All quantitative data is collated with clinical descriptors. Please see methods section under specimen collection for details regarding the selection of individual samples for each experiment.

In total 34 samples were genotyped for a polymorphism within CTCF BS6 and parental contributions were determined for heterozygotes (see FIG. 2 and bisulfite sequencing methods for details.) Only lesions of the head and neck were included. Of these samples, 3 were excluded because they were not on the head or neck. Two other samples were excluded because one was not Glut-1 positive on histology and one had a previous resection of the same lesion prior to evaluation, (See FIGS. 10A to 10D for details.) Thus 29 individuals were included in this analysis. Charts were retrospectively reviewed from patients treated either at the Yale University Plastic Surgery Center (New Haven Conn.), or the Vascular Birthmarks Institute (New York, N.Y.). The age of the lesion was then compared to the size of the lesion as determined below. These data were plotted and separated by CTCF BS6 genotype and parental contribution in heterozygotes. ANCOVA analyses were then performed on putative growth curves. The age at the time of resection, with corresponding size, was used only for proliferating lesions. For those lesions that were resected at the time of involution, or quiescence, the size of the lesion at the clinical visit where quiescence was first noted was used. In the case of medical interventions, the size of the lesion before a response was noted was used. This information was used to create a clinical table of results were factors such as ulceration, steroid/chemotherapeutic, and laser treatment were also noted (note that no beta blockers were used in the sample population.) Thus, different ages are associated with most individuals when comparing the clinical data table and the master data table. For instance: Sample #7 has an age of 2304 days assigned in the Master Data Table, shown in FIGS. 10A to 10D. However, in the Clinical Table the age assigned to sample #7 is 1050 days. The difference in age assignments represent the age of the patient when the lesion was excised (this age was used for the molecular analyses) versus the age of the patient either before the first response to medical intervention was noted or when the lesion first entered the quiescent phase. Thus, for sample number 7: The lesion entered the quiescent phase (as determined retrospectively) at age 1050 days but was then excised at age 2304 days. Regarding the assessment of lesion size, if multiple dimensions were given, the largest was used. In some cases, only one dimension was given so volumetric estimations could not be calculated for every patient. Thus, patients' lesions were standardized to a greatest diameter equivalent. This measurement was correlated with clinical photographs when available. All data utilized varied by less than 10% between stated measurement and photographic estimation when available. Lesions were classified into one of three growth phases: proliferative, quiescent and involuting. Only sizes of lesions that were in the proliferative or quiescent phase were used in this study. All data was stored in a de-identified format with a unique accession number for each patient.

DDNA Preservation and Extraction

Immediately following tissue resection, DNA was isolated using the Qiagen DNeasy Tissue Mini Kit according to the manufacturer's protocol. Only samples with an A260/A280 measurement of 1.8 or above that ran as a single band on the gel were further analyzed.

FIG. 2. Deducing Parental Contributions From Direct Sequencing and Bisulfite Pyrosequencing. FIG. 2: 29 patients were genotyped via direct sequencing of blood samples for a known polymorphism within the core CTCF BS6 sequence (rs10732516.) All homozygous genotypes could be deduced from this information alone. FIG. 2B: All samples (heterozygotes and homozygotes) were subjected to bisulfite conversion and quantitative methylation sensitive pyrosequencing. Methylation occurs only on the paternal chromosome for CTCF BS6. In normal tissue, such as patient matched control blood, this assay is capable of isolating the genotype of the paternal chromosome. As thymidine cannot be methylated, those individuals with a paternal T at rs10732516 were not methylated at CpG#5. Paternal C carrying individuals were methylated at CpG#5. Thus, the maternal and paternal contribution to CTCFBS6 can be deduced. This assay sidesteps the need for directly sequencing parents' DNA and eliminates the potential ambiguity ensuing from heterozygous parents. Note: The methylation values of this assay are subject to primer bias, Tost et al (25.) This is evident by the 3 distinct groupings of methylation levels, which are artifactual.

RNA Preservation and Extraction

Immediately following tissue resection, 100-500 mg of tissue was stored in Quiagen RNA Later solution according to the manufacturer's protocol. RNA was extracted via liquid nitrogen powder homogenization using Invitrogen Trizol reagent according to the standard protocol. 10 μg of total RNA from each sample was then treated with DNase Qiagen mini-elute columns according to manufacturer's specifications. RNA integrity was then assessed using Agilent bioanalyzer 2100 (provided as a service of the Keck Center at Yale University.) Those samples with 18s/28s ratio of 1.8 or greater were converted into cDNA using the ABI 4368813 cDNA archive kit. All samples were then stored at −80 degrees C.

Quantitative rtPCR for CTCF, BORIS, H19 and IGF2

Nineteen IH samples with suitable RNA, as previously specified, were subjected to fluorescent quantitative RT-PCR using ABI Taqman primers that were previously validated by the manufacturer and spanned intron exon boundaries. For reasons of sample scarcity, not all samples were subjected to each assay (See FIG. 1 for details.) The assays were: IGF2—assay number Hs00171254_m1, H19—assay number Hs00399294_g1, CTCF—assay number Hs00198081_m1, and BORIS—assay number Hs00540744_m1. Gene quantification was performed using the standard curve method via pooled sample cDNA (equal contributions from each sample) and successive two fold dilutions, beginning from 50 ng and ending with 0.39 ng. All reactions were performed on the ABI 79005 thermocycler using default cycling conditions previously optimized for these assays. Reactions were performed in duplicate and average CT values, if they agreed within 0.4 cycles, were used to calculate absolute quantity. Three runs of RT PCR were performed with overlapping samples in each run to allow normalization of the data. Not all samples were subjected to every assay depending upon sample quantity. Of Note: Sample #4 does not have an H19 transcription value, as on duplicate plating for rtPCR, the CT values did not agree within 0.4 cycles. Furthermore, samples 15-19 were the final rtPCR of the three runs performed and due to sample scarcity and the need to construct standard curves from pooled samples, only CTCF and BORIS rtPCR's were performed.

Western Analysis 24 samples were subjected to Western analysis. As this process is tissue intensive, younger samples such as #21 and #23 could only be used for this analysis as insufficient tissue was left for further processing. Other samples were selected biased toward analyzing those samples with transcriptional data in order to compare transcriptional phenomena to translational. However, as the analysis proceeded, presentation gels were constructed to demonstrate key transition points in CTCF and BORIS translation in samples that had not been treated with steroids. Briefly, 50 mg of each sample were processed with a rotary homogenizer in 200 ml of RIPA lysis buffer. After centrifugation lysates were created using a standard beta-mercapto-ethanol with SDS. PAGE was performed with 36 μg of protein per well in NuPage 10% Bis-Tris precast gels in MOPS buffer at 100 volts. PAGE separated proteins were then transferred for two hours to a PVDF membrane (Bio-Rad) in a standard transfer buffer at 100 mAmps. Anti BORIS antibody (Abcam 18337) was used at 1/5000 dilution in TBST with 5% cows milk overnight. Two concentrations of anti-CTCF were used—1: 10,000 and 1:5,000—to better visualize late and early rises in CTCF protein (see FIG. 3 legend for details.) As anti-CTCF and anti-BORIS were both rabbit polyclonal antibodies they could be visualized simultaneously on the same film following incubation with the anti-rabbit secondary conjugated to horseradish peroxidase and ECL treatment. Images were then scanned and adjusted for brightness and contrast in Adobe Photoshop.

Bisulfite Methylation Analysis Using Quantitative Pyrosequencing

This method was first described by Grunau et al and Dupont et al. Incomplete bisulfite conversion was detected by designing amplicons that contained at least 1 unmethylated cytosine. Primer bias was controlled for by establishing methylation curves of 100% methylated DNA titrated against known amounts of whole genome amplified PCR products that, by definition, are unmethylated. These methylation curves allow experimental samples to be calibrated against known standards. The presence of an A/G polymorphism, approximately 130 base pairs downstream of CTCF BS6 leads to primer bias and distorts the absolute methylation values of CTCF BS6, Tost et al.

Deducing Parental Contributions of Alleles at CTCF BS6

All samples were subjected to direct sequencing of CTCF BS6 containing the polymorphism rs10732516. The DNA samples were subjected in parallel to methylation sensitive pyrosequencing of the same polymorphism; please see the section titled "Specimen Collection" for further details. Comparing these results allows each parental contribution to be deduced, see FIG. 1 for full details.

Figure 3A:
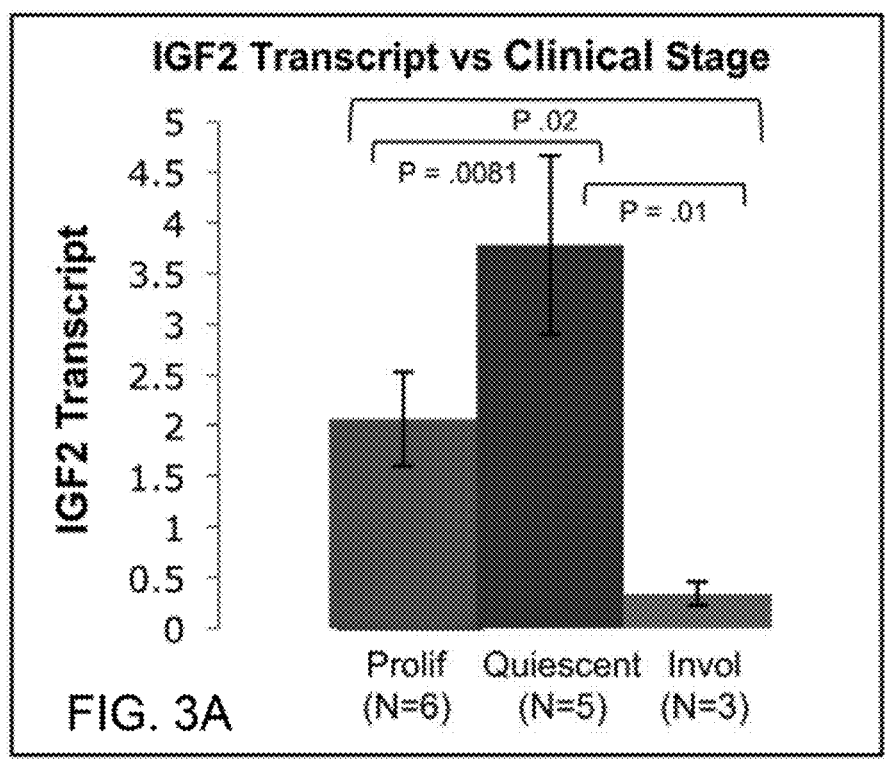
Figure 3B:
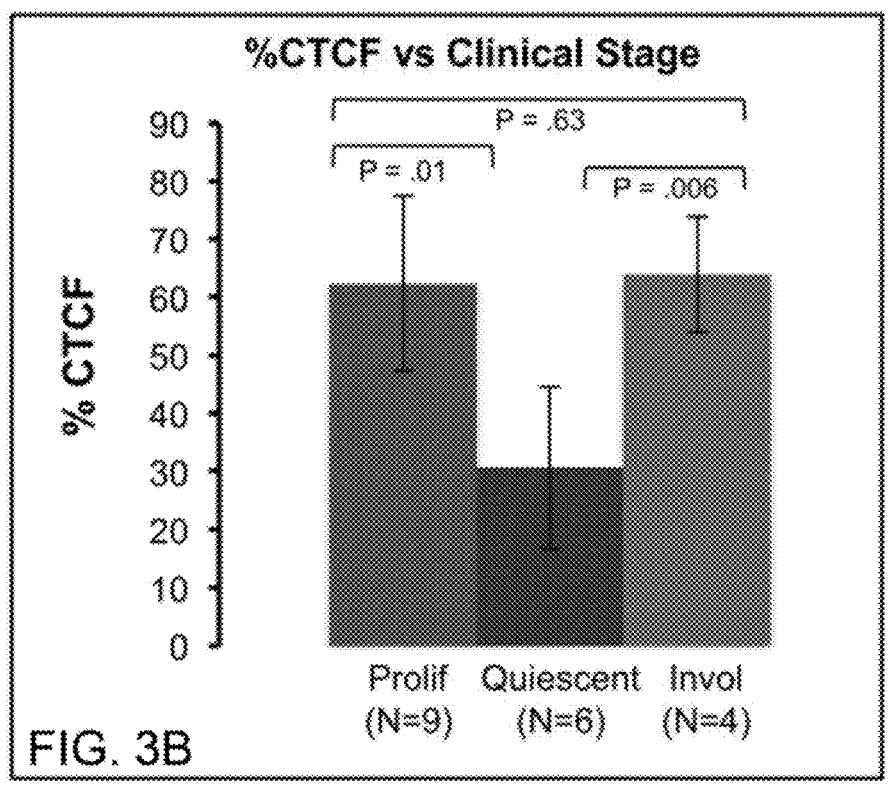

As shown in FIG. 3, IGF2 transcription by clinical stage shows an inverse relationship to the % CTCF of identical stage. FIG. 3A: IGF2 mRNA levels were approximately 6× lower in the involuting samples compared to their proliferating counterparts. Proliferating vs. involuted p=0.02, Proliferating vs. quiescent p=0.0081, Quiescent vs involuting vs. involuting p=0.01. Wilcoxian Rank Sum Test. Error bars represent standard deviation. FIG. 3B: % CTCF changes significantly according to clinical stage. Prolif vs. quiescent p=0.01, quiescent vs. Invol p=0.006, prolif vs. invol p=0.63, Wilcoxian two sample test. Error bars represent standard deviation. Note: All samples in the IGF2 analysis were included in the % CTCF analysis, with additional samples.

Genomic Southern Analysis for the H19 Promoter

Eighteen were analyzed at a CLIA certified molecular diagnostics laboratory where this assay is performed as a clinical test for Beckwith-Wiedemann Syndrome. The assay is originally described by Debaun et al. Norms for this test were previously established with 30 normal controls at 55% methylation with a standard deviation of 5%. All samples were run with a normal and Beckwith-Wiedemann control. The assay exploits a CCCGGG site in the H19 promoter that is cut by the methylation sensitive restriction enzyme Pst1.

Statistical Analysis

Descriptive statistics were used to present patient characteristics. The difference in expression of IGF2 transcript across the three developmental stages of IH was evaluated using a Kruskal-Wallis test. To evaluate if the relative amount of CTCF compared to BORIS transcript changes predictably over time, change point analysis was performed. Change point analysis indicates the likelihood that a change in transcript expression occurred in the sample population by confidence level and a confidence interval regarding when those changes occur. The % CTCF [CTCF/(CTCF+BORIS)×100] was used to develop a change point model that was then compared against clinical staging and IGF2 expression in the sample population. A full explanation of the methods used, as well as a shareware change-point analyzer is presented as an online resource: Taylor, Wayne A. (2000), "Change-Point Analysis: A Powerful New Tool For Detecting Changes," (http://www.variation.com/cpa/tech/changepoint.html.) To evaluate the association of IGF2 transcript and the relative amounts of CTCF, a linear regression model was fitted, with the % CTCF and age as covariates. The correlation and partial correlation were also calculated. Partial correlations indicate what percentage of variance in IGF2 can be explained by CTCF % alone. Analysis of the covariance model (ANCOVA) was fitted to examine if the correlation between the IGF2 transcript and the difference between CTCF and BORIS varied by the paternal genotype at CTCF BS6, once adjusted by age.

Results Master Data Table

In total, 40 samples were analyzed on a molecular basis. A description of basic demographics, with genotypes at CTCF BS6 and transcript expression values for IGF2, H19, CTCF and BORIS with correlative methylation data was compiled. Please see FIGS. 10A to 10D: Master Data Table for details. This table can be utilized to confirm any statistical analysis presented in this study.

Expression of IGF2, CTCF and BORIS

Figure 4A:
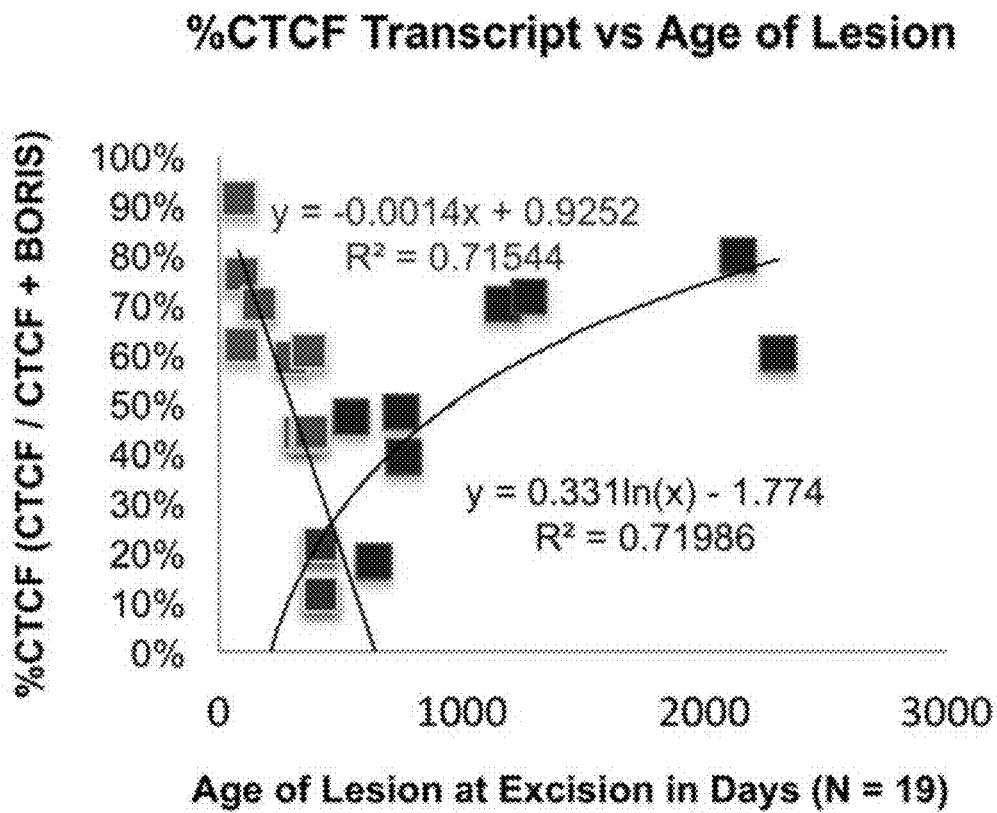
FIG. 4A shows a graph of the percent CTCF with respect to CTCF and BORIS versus the age of the lesion.
Figure 4B:
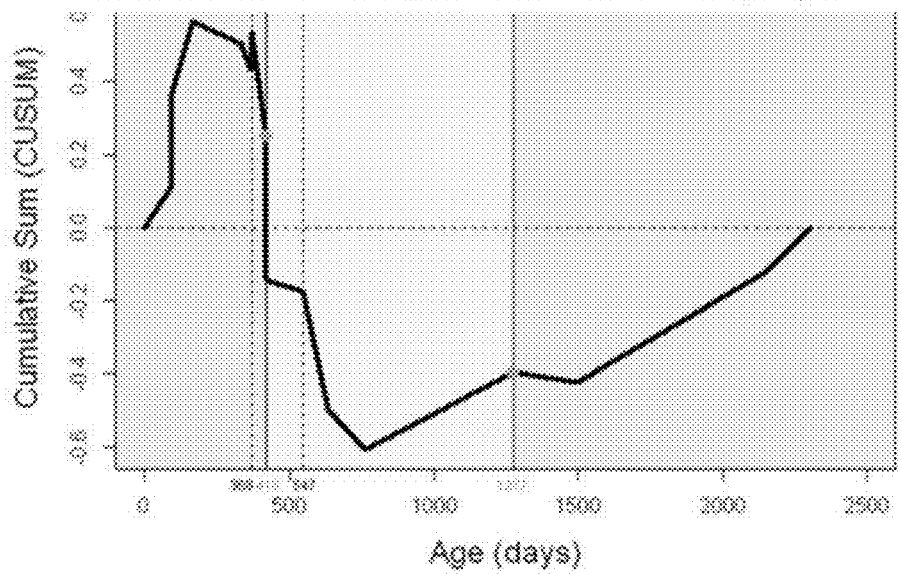
FIG. 4B shows the CSUM of % CTCF versus the age of the lesion.

FIGS. 4A and 4B Analyzing the Percentage of CTCF Compared to Total CTCF and BORIS Transcript.

FIG. 4A Using the two samples with the lowest % CTCF (420 and 418 days as common points (Purple)) two curves with high correlation to age can be appreciated. % CTCF steadily decreases as lesions age until approximately 400 days (red and purple points), then CTCF once again increases compared to BORIS (purple and blue points). This roughly correlates with the transition from proliferative to quiescent lesions. FIG. 4B CSUM of % CTCF demonstrates statistically significant variation about the mean of % CTCF according to age. For a full explanation of the CSUM data and commensurate change point analysis.

IGF2 transcription differed significantly by clinical stages (p<0.0001, Kruskal-Wallis test). Plateau stage lesions expressed significantly higher levels of IGF2 than proliferating (p=0.0081, Wilcoxon rank sum test) and involuted samples (p=0.02). Involuted hemangiomas expressed the lowest levels of IGF2, approximately 6× lower than their proliferating counterparts (p=0.01).

To potentially explain the changes in IGF2 transcription, quantitative RT-PCR was performed for CTCF and BORIS. CTCF and BORIS are co-expressed in all samples. However, the percentage of CTCF transcript compared to total CTCF and BORIS in a given sample [CTCF/(CTCF+BORIS)×100] varied significantly over developmental time (FIGS. 3B and 4A). This was confirmed by a change point model (FIG. 4B): the Y axis is the cumulative sum (CUSUM) of the differences between % CTCF and the average value of % CTCF. A segment of the CUSUM chart with an upward slope indicates a period where the values tend to be above the overall average. Likewise, a segment with a downward slope indicates a period of time where the values tend to be below the overall average. Based on this analysis, two change points, one estimated at 418 days and the other at 1277 days, were detected. Prior to approximately 418 days (90% CI: 368-547 days), the value of % CTCF tends to maintain a higher level with an average value in this stage equal to 59%. In the second stage (418-1277 days), the level of % CTCF is low with an average 28%. After the second change point at approximately 1277 days (90% CI: 760-1500 days), % CTCF has recovered to a high level again with the average 66%. This result is highly similar to the results obtained by separating samples according to clinical stage % CTCF transcription in IH varies according to clinical stage (FIG. 3B) Furthermore, the % CTCF varied inversely with IGF2 transcription (compare FIGS. 3A and 3B) These two graphs dearly demonstrate that a higher % CTCF corresponds with lower levels of IGF2 expression. Moreover, a strong positive correlation was detected between BORIS and IGF2 transcription (p=0.0028). Though CTCF alone does not significantly correlate with IGF2 transcript levels, taking both CTCF and BORIS into account using % CTCF is the strongest predictor of IGF2 mRNA expression p=0.0004 (FIG. 5).

Figure 5:
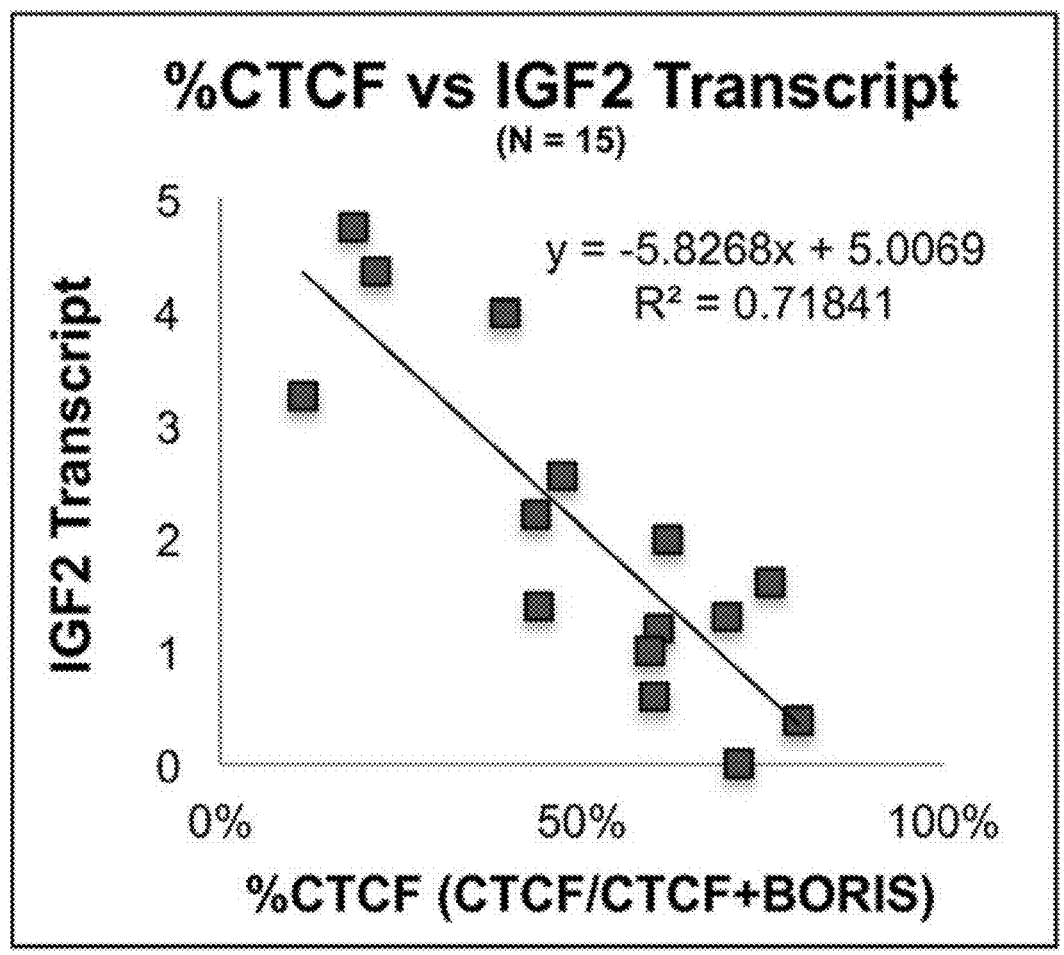
FIG. 5 shows a graph of IGF2 Transcript versus the % CTCF.

As described herein, a reduction, especially a rapid reduction, in the % CTCF, as expressed in FIGS. 4A, 4B, and 5, may be an indication of an aggressive tumor and may be used to risk stratify the patient. A % CTCF may be determined as a proportion of the sum of the expression level of CTCF and expression level of BORIS. It has been found that a reduction in the % CTCF overtime, or rate of % CTCF, in indicative of a more aggressive tumor, thereby putting the patient in an higher risk classification. For example, as shown in FIG. 4A, if the line fit of % CTCF versus age in days has a negative slope, then a patient may be classified in as a highest risk patient and if the slope is positive, then the patient may be classified as a lowest risk patient.

As shown in FIG. 5, IGF2 transcript levels correlate inversely with the percentage of CTCF compared to a total of CTCF+BORIS. This data represents the first demonstration of the potentially antagonistic effects of CTCF and BORIS on a target gene's transcription through a continuous curve. P=0.0004 ANCOVA Model. Age effect was not significant in the model p=0.241. The % CTCF is a stronger statistical predictor of IGF2 expression than BORIS alone 0.0004 vs. 0.0028 respectively. (N=15)

Figure 6:
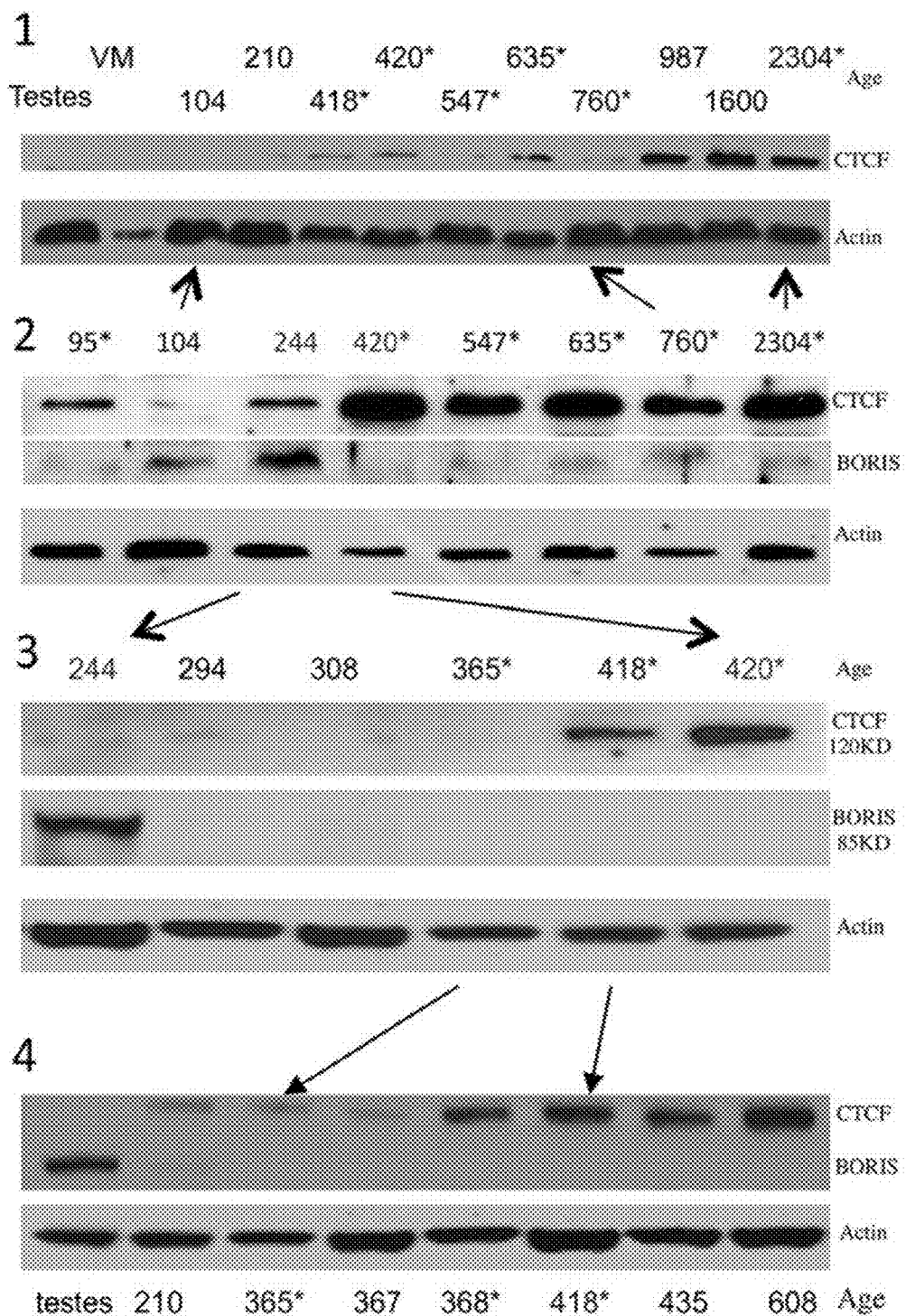
FIG. 6 shows Western Analysis of 24 IH Samples Via 5 Independent Western Blots.

FIG. 6, shows Western Analysis of 24 IH samples via 5 independent Western Blots. Twenty samples with 4 blots depicted, demonstrates 4 stages of CTCF and BORIS expression. 6-1: A low concentration of anti-CTCF (1:10,000) demonstrates the complete spectrum of CTCF expression with increases early (210 to 418) and late (760 to 987) in protein expression. (Note, a testes negative control was included as well as a venous malformation denoted as "VM.") 6-2 through 6-4 were probed with 1:5000 concentration of anti-CTCF that more clearly demonstrates the early rise in CTCF that occurs after 367 days. 6-2 suggests an early increase in BORIS with precipitous downregulation after 244 days. 6-3 and 6-4 expand this critical age range demonstrating a period from 244 days to 367 where BORIS is downregulated but CTCF is not yet upregulated. Note, samples marked with an asterisk were also subjected to CTCF and BORIS rtPCR.

Western analysis of CTCF and BORIS confirms and expands upon the transcript data (FIG. 6) As expected in proliferating lesions, BORIS transcript and protein levels steadily rise in early stage samples (FIG. 4A transcript data, FIG. 6-2 Western Analysis.) Furthermore, during the transition from quiescent to involuting samples, CTCF mRNA and protein increase compared to BORIS (FIGS. 3B, 4A and 4B transcript, and FIG. 6-1 protein.) Thus, the western and transcriptional data globally confirm one another at the endpoints of IH development. However, the protein data suggests a third change in CTCF and BORIS levels that the transcript change point analysis does not. This third proteomic change appears to take place at the late proliferating to early quiescent phase. It coincides with the so-called late proliferative stage in IH that is suggested by clinicians but not universally accepted. These data provide the first molecular support for what was previously a clinical category: the late proliferative stage of IH growth. The relative expression of CTCF and BORIS via both transcript and protein levels, is predictive of clinical stage and IGF2 expression. See FIG. 7 for details.

Figure 7:
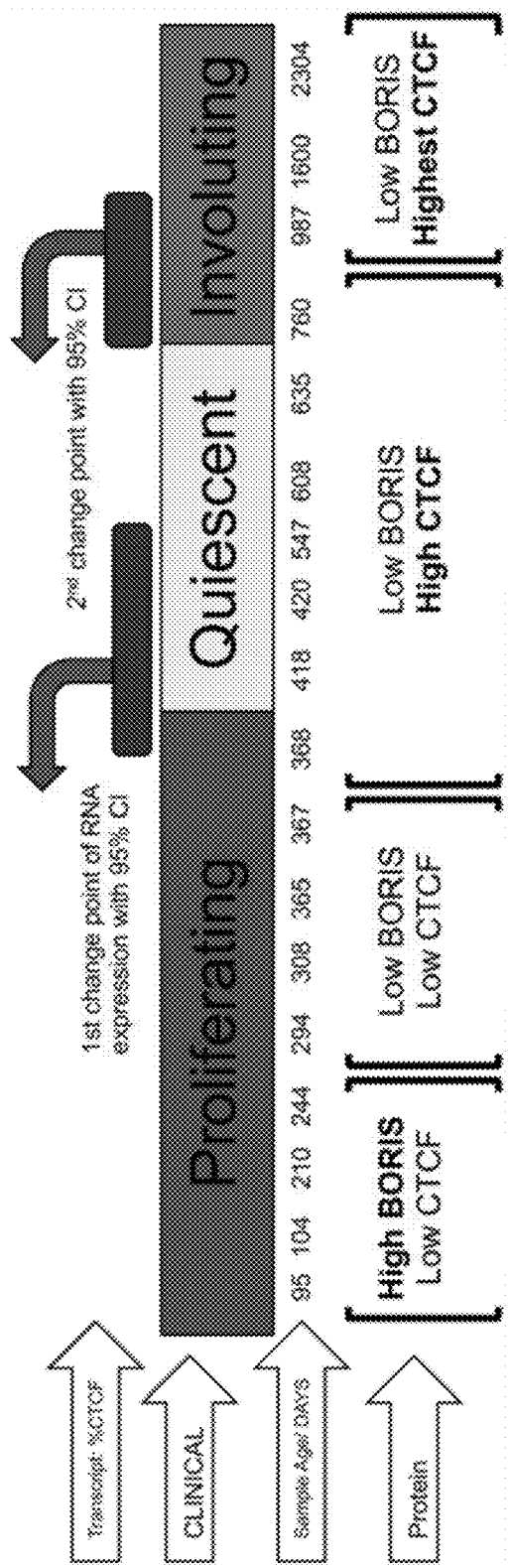
FIG. 7 shows a schematic integrating CTCF and BORIS expression via both transcript and protein with clinical stage.

FIG. 7. shows a schematic integrating CTCF and BORIS expression via both transcript and protein with clinical stage. The Western analysis suggests 4 stages of CTCF and BORIS (see FIG. 3, panels 1 to 4) each stage leading to higher levels of CTCF expression relative to BORIS. These interval changes in protein expression closely correlate with clinical stage. Furthermore, bars above the stages represent the 95% confidence intervals of the two change points identified by quantitative rtPCR. These data show remarkable agreement reinforcing the idea that relative CTCF and BORIS expression levels closely mirror the clinical stage of the lesions tested. Of note, the CTCF and BORIS protein data also suggest a molecular basis for a late proliferative stage.

Figure 8B:
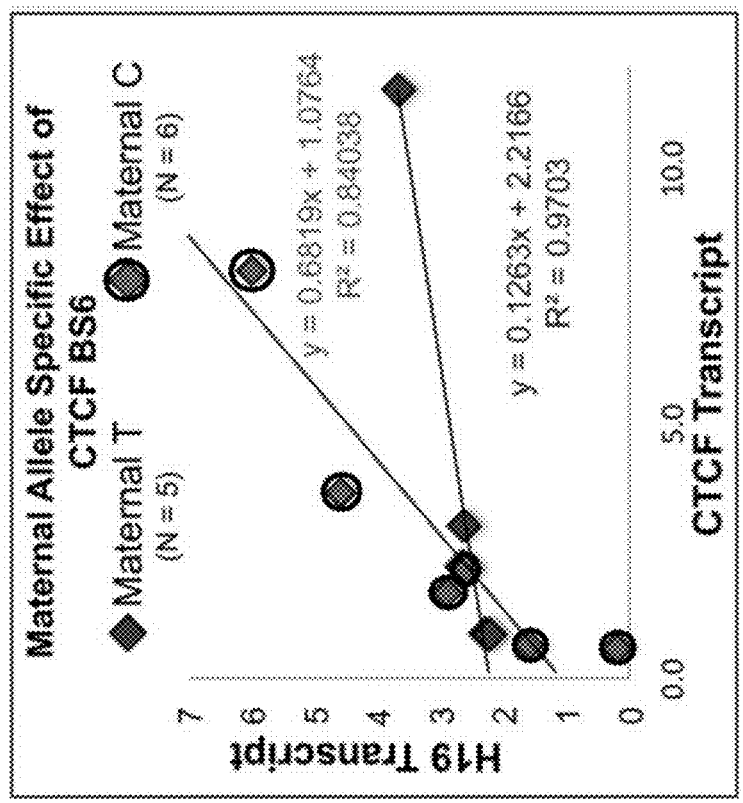

The CTCF to BORIS transcript difference (C-B) predicts IGF2 transcription according to the paternal allele at CTCF BS6. This study utilizes existing technologies: Direct sequencing of the known polymorphism of CTCF BS6 (rs10732516) with a previously described methylation assay for CTCF BS6. Applying these two assays in a novel manner (see FIG. 2) allowed us to deduce both maternal and paternal contributions to CTCF BS6—which will be referred to as the maternal and paternal contribution (FIG. 8.) This paternal contribution likely has significant effects on IGF2 production as it relates to CTCF and BORIS.

IGF2 mRNA is demonstrated to be inversely related to CTCF and positively correlated to BORIS transcripts when plotted against % CTCF (FIG. 5).

Figure 8A:
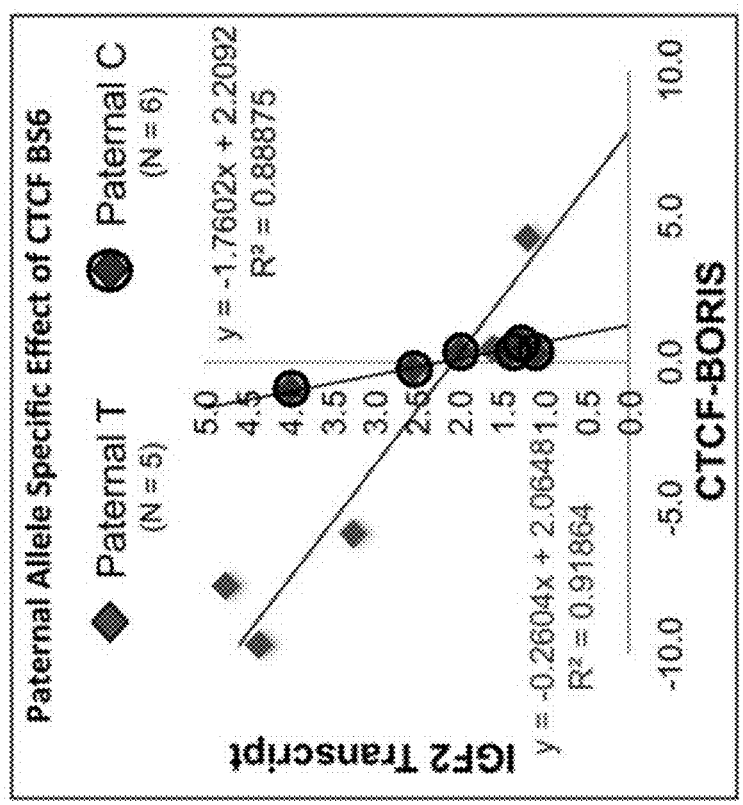

By using the difference between CTCF and BORIS (C-B) rather than the % CTCF, this relationship can be differentiated by the paternally contributed allele at CTCF BS6 (FIG. 8A). The paternal allele of a common C/T polymorphism within CTCF BS6 (rs10732516) corresponds with two strikingly different CTCF-BORIS vs. IGF2 curves. After age adjustment, the effect of CTCF-BORIS on IGF2 transcription was significantly different between patients bearing different paternal alleles (p=0.05, ANCOVA model) and there is a strong correlation between IGF2 expression and CTCF-BORIS (p=0.0007). The samples bearing a paternal C allele, appear to demonstrate a six fold steeper slope of IGF2 mRNA relative to the CTCF-BORIS difference, compared to their paternal T bearing counterparts. This allele was identified in both tissue and patient matched control blood. Of note, heterozygote analysis revealed no clear relationship regarding these factors according to the maternal allele (p=0.95, ANCOVA model). It remains a possibility that the paternal allele effect may be steroid treatment driven as more samples with the paternal T allele were treated with steroids than the paternal C allele. This potential bias was investigated with an odds ratio calculation sorting steroid treatment according to paternal genotype. The odds ratio suggested that paternal T samples were more likely to be treated with steroids but this result did not reach statistical significance. As the allele specific analysis was done on only proliferative samples the odds ratio calculation was performed twice, once including involuted samples and once to their exclusion. However, it is acknowledged that the odds ratio suggested a potential steroid treatment bias in paternal T samples, which may have become significant in a larger patient cohort. Lastly, IGF2 expression in IH was mono-allelic in all 5 informative heterozygotes tested for a known IGF2 polymorphism in exon 9. IGF2 imprinting status appears to be maintained despite BORIS expression.

H19 transcript levels correlate positively with CTCF mRNA according to the maternally contributed allele at CTCFBS6. After age adjustment, CTCF transcript levels alone correlated positively with H19 transcription but only when separated by maternal genotype ((p=0.0150, FIG. 8B) Moreover, this positive correlation is significantly different among patients with different maternal alleles (p=0.0129, ANCOVA). The correlation between CTCF and H19 transcription is stronger in patients bearing a maternal C allele compared to their maternal T counterparts. There were no identifiable relationships between H19 transcription and either the paternal genotype at CTCF BS6 or BORIS mRNA, p=0.8 ANCOVA. There also appeared to be no relationship between H19 expression and clinical stage of the hemangioma.

It remains a possibility that the maternal allele effect may be steroid treatment driven as more samples with the maternal T allele were treated with steroids than the maternal C allele. This potential bias was investigated with an odds ratio calculation sorting steroid treatment according to maternal genotype. The odds ratio suggested that maternal T samples were more likely to be treated with steroids but this result did not reach statistical significance. it is acknowledged that this odds ratio may have become statistically in a larger sample size; the effect was not great enough to significantly bias the sample size.

Multiple imprinted sites within the IGF2/H19 locus are abnormally methylated in IH compared to matched control blood.

It remains a formal possibility that the normalization of CTCF to BORIS ratios, as well as decreased IGF2 transcription, in involuting and involuted samples is not due to an intracellular phenomenon but rather the incremental replacement of abnormal IH tissue (vascular stroma) with normal tissue (fat.) Thus, the results presented are the product of tissue heterogeneity. It is acknowledged that IH lesions transform from a vascular tumor into a fibrofatty residuum; therefore, the transitional phases are by definition composed of heterogeneous cell populations. However, no evidence was observed that the fibrofatty residuum of an involuted IH represents "normal" tissue. To the contrary, many of the methylation abnormalities discovered by this study are either stable or progressive from early to late clinical stages. For instance, the H19 promoter is significantly demethylated in all IH samples. However, the demethylation is progressive with age. Furthermore, it was also found focal demethylation at Exon 9 and hypermethylation at DMR0, deviating from the expected 50% for these known imprinted sites. Both findings remained consistent in all IH clinical types and were age independent. If IH tissues were being replaced by normal fat it would be expect the methylation abnormalities demonstrated in this work to normalize, not remain constant or even progress with age. Given this argument, the simplest explanation for the methylation data is that IH tissue begins as epigenetically abnormal vascular stroma and transforms into epigenetically abnormal fat or is at least replaced by the like.

CTCF BS6 Genotypes Correlate with Clinical Outcomes

Figure 9A:
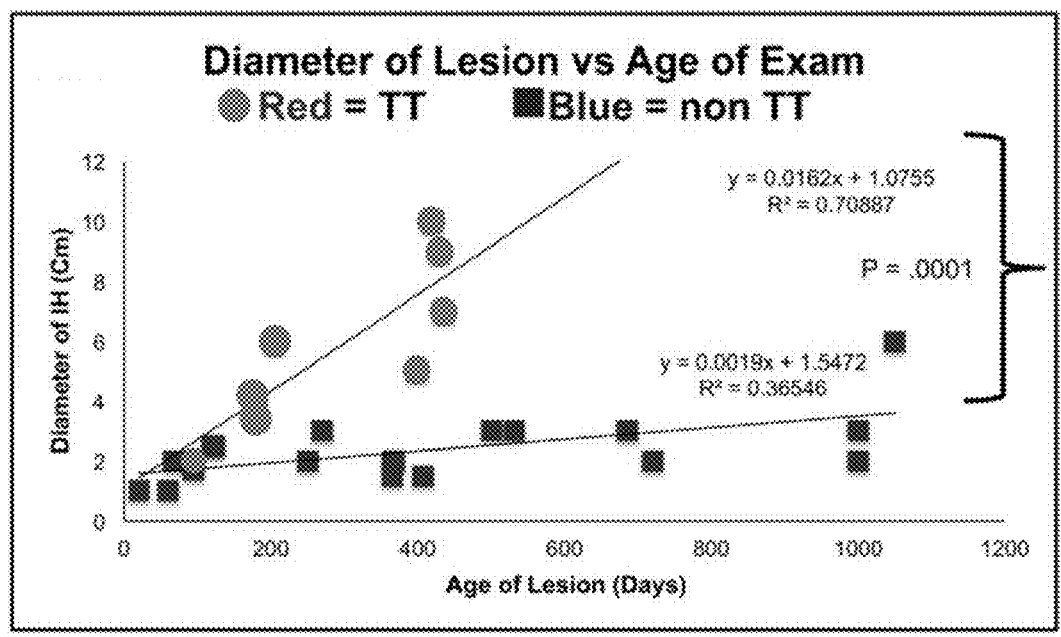
FIG. 9A shows a graph of the diameter of an infantile hemangioma versus the age of the lesion in days for TT and non-TT patients.
Figure 9B:
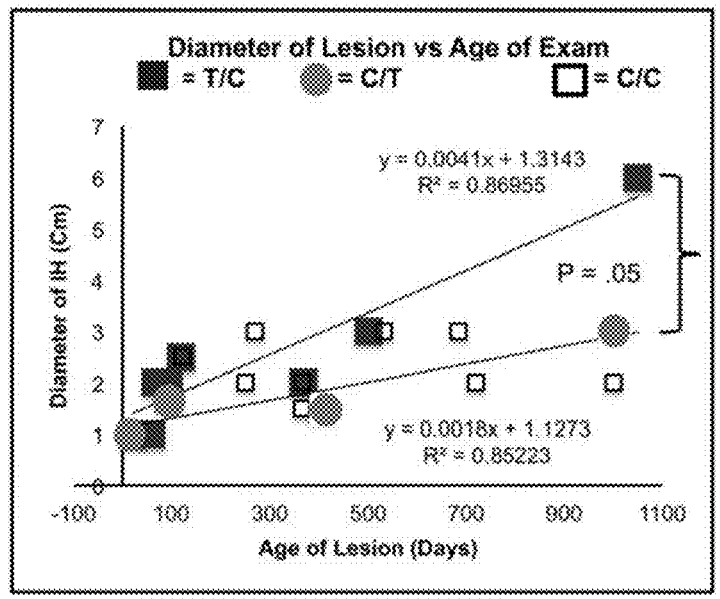
FIG. 9B shows a graph of the diameter of an infantile hemangioma versus the age of the lesion in days for TC, C/T and C/C patients.

Mechanisms aside, parent of origin specific effects are demonstrated at the molecular level regarding expression patterns of both IGF2 and H19. However, the question remains whether these molecular phenotypes may translate into clinically significant growth patterns. FIG. 12 is a complete table of all patients participating in this retrospective clinical study. For details of subject inclusion please see methods section. Size of the lesion as well as the date of examination was included with relevant clinical information such as sex, medical treatments utilized and presence of ulceration during clinical course. Each patient was sorted according to CTCF Binding Site Six Genotype and paternal contribution for heterozygotes. By plotting the size of IH lesions against the CTCF BS6 genotypes, four distinct growth curves emerge (FIGS. 9A and 9B).

As shown in FIG. 12, many of the patients were treated with a cortical steroid-methyl pregnisone, either by injection or systemic oral intake. Table 1 shows that the patients with a non-TT allelic expression had a much better response to this medication, wherein only 25% had a failure of response to the medication. In contrast, the patients with aa TT allelic expression had the least effective response to the Cortical steroid treatment.

TABLE 3

| Allelic Expression | Failure of Steroids | Non-Failure of Steroids |
|---|---|---|
| TT | 7 | 2 |
| Non-TT | 5 | 15 |

The results of this analysis shows that the type of allelic expression can be used to predict the effectiveness of Cortical steroid treatment. The odds ratio from this stud is 10.5 that the TT group will fail steroids, with a sensitivity of 58.33% (95% CI 27-84%) and a specificity of 88.33% (95% CI 63-98%). The failure of steroids is defined in this analysis as the patient requiring surgical treatment despite the treatment with the medication, cortical steroids.

FIG. 9. Clinical Correlation of Hemangioma Growth Rates with Parental Contributions to CTCF BS6. FIG. 9A:

This retrospective analysis of 29 samples, 9 TT, 20 non TT, demonstrates significantly distinct growth curves over a large age range. The ANCOVA model has identified age as a predictor of size p=0.0007. The association between tumor size and age is significantly different among the genotypes of TT, C/T, T/C and CC p<0.0001. Of Note the paternal contribution is presented first and the maternal is second. The interaction terms of parentally specific genotypes allowed us to test if the slopes of the curves between tumor size and age are different among the genotypes. This analysis indicted that an increase in 1 day of age is associated with 0.016 cm of growth in the TT group. This is significantly higher than the non TT group p=0.0019. FIG. 10B: Growth analysis focusing on the "non TT" group. Each non TT growth curve varied independently and significantly from the TT samples (CC vs. TT: P<0.0001, CT vs. TT: P<0.0008, TC vs. TT: P=0.0025). Furthermore, these data suggest parent of origin specific effects as those samples with identical genotypes but opposite parental contributions displayed statistically significant differences in growth curves. The paternal T/maternal C genotype grew at approximately twice the rate as their paternal C/maternal T carrying counterparts (p=0.05). The homozygous C group appeared to have a roughly flat growth rate between the heterozygotes and did not significantly vary with either heterozygote group (CC vs. C/T p=0.99, CC vs. T/C p=0.74)

The association between tumor size and age (days) are significantly different among these four genotypes (separating heterozygotes by their respective parental contributions) CC, C/T, T/C. TT (p=0.0162, ACOVA.) The most impressive growth phenotype was exhibited by homozygous T samples reaching an average of 7.8 cm before excision (FIG. 9A) Comparing the TT group against all non-TT subjects, the difference in lesion size, increased significantly with age (p=0.0001, ANCOVA). Thus in this study, TT lesions grew more rapidly than non-TT genotypes. In fact, each growth curve-separated by maternal and paternal genotype-varied independently and significantly from the TT samples (CC vs. TT: P<0.0001, CT vs. TT: P<0.0008. TC vs. TT: P=0.0025). Although genotype appears to have no effect at approximately 100 days, after three months, lesions begin to distinguish themselves suggesting distinct growth velocities. Furthermore, these data suggest parent of origin specific effects as those samples with identical genotypes but opposite parental contributions displayed statistically significant differences in growth curves. Namely, those lesions carrying the paternal T/maternal C genotype grew at approximately twice the rate as their paternal C/maternal T carrying counterparts p=0.05 (FIG. 10B) Furthermore, each heterozygote growth curve varied by age with high correlation of r squared above 0.85. However, it must be emphasized that sample size is relatively low (particularly in the C paternal/T maternal group) and the p-value just reached the threshold of significance.

TT Lesions Have a Significantly Higher Associated Odds Ratio for Ulceration. This proposed clinical test could be most useful in ruling out the chance of ulceration early in the disease course as sensitivity and negative predictive value are high. A larger prospective study is warranted.

Lastly, size is a highly significant clinical outcome when studying IH. However, of similar importance is ulceration. Once an IH ulcerates, it is usually painful for the patient and is given to bleeding which can be clinically significant. Ulceration is usually a marker of rapid disease progression and heralds an escalation of care. This can entail the institution of laser therapy, pharmacologic intervention or surgical excision. Not surprisingly, ulceration alone can prompt surgical treatment regardless of size or location of the lesion. To study the risk of ulceration an odds ratio calculation was performed comparing TT and non-TT lesions. The TT lesions had an odds ratio of 76.1 for ulceration p=0.006 (FIG. 13. Although this is a small sample cohort preliminary specificity was performed, sensitivity and positive and negative predictive value calculations (FIG. 13. These early results suggest the highest clinical usefulness of the proposed test in ruling out potential future ulceration. Although encouraging, these results will need to be corroborated prospectively in a larger cohort.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

The following references are hereby incorporated by reference in their entirety:

REFERENCES

1. Mulliken J B, Glowacki J (1982) Hemangiomas and vascular malformations in infants and children: a classification based on endothelial characteristics. Plastic and reconstructive surgery 69: 412-422. PMID: 7063565
2. Mulliken J B, Glowacki J (1982) Classification of pediatric vascular lesions. Plastic and reconstructive surgery 70: 120-121. PMID: 7089103
3. Glowacki J, Mulliken J B (1982) Mast cells in hemangiomas and vascular malformations. Pediatrics 70: 48-51. PMID: 7088632
4. North P E, Waner M, Brodsky M C (2002) Are infantile hemangioma of placental origin? Ophthalmology 109: 223-224. PMID: 11825799
5. North P E, Waner M, Mizeracki A. Mrak R E. Nicholas R, et al. (2001) A unique microvascular phenotype shared by juvenile hemangiomas and human placenta. Archives of dermatology 137: 559-570. PMID: 11346333
6. North P E, Waner M, Mizeracki A, Mihm M C J (2000) GLUT1: a newly discovered immunohistochemical marker for juvenile hemangiomas. Human pathology 31: 11-22. PMID: 10665907
7. Chang L C, Haggstrom A N, Drolet B A, Baselga E, Chamlin S L, et al. (2008) Growth Characteristics of Infantile Hemangiomas: Implications for Management. Pediatrics 122: 360-367. doi: 10.1542/peds. 2007-2767 PMID: 18676554
8. Ritter M R, Dorrell M I, Edmonds J, Friedlander S F, Friedlander M (2002) Insulin-like growth factor 2 and potential regulators of hemangioma growth and involution identified by large-scale expression analysis. Proceedings of the National Academy of Sciences of the United States of America 99: 7455-7460. PMID: 12032304
9. Yu Y, Wylie-Sears J, Boscolo E, Mulliken J B, Bischoff J (2004) Genomic imprinting of IGF2 is maintained in infantile hemangioma despite its high level of expression. Molecular medicine (Cambridge, Mass. 10: 117-123.
10. Weksberg R (2003) Beckwith-Wiedemann syndrome demonstrates a role for epigenetic control of normal development. Human molecular genetics 12: 61R-68. doi:10.1093/hmg/ddg067

11. DeBaun M R, Niemitz E L, McNeil D E, Brandenburg S A, Lee M P, et al. (2002) Epigenetic alterations of H19 and LIT1 distinguish patients with Beckwith-Wiedemann syndrome with cancer and birth defects. American journal of human genetics 70: 604-611. PMID:11813134
12. Ferguson-Smith A C, Surani M A (2001) Imprinting and the epigenetic asymmetry between parental genomes. Science 293: 1086-1089. PMID: 11498578
13. Reik W, Walter J (2001) Genomic imprinting: parental influence on the genome. Nature reviews 2: 21-32. PMID: 11253064
14. Chemukhin I. Shamsuddin S, Kang S Y, Bergstrom R, Kwon Y W, et al. (2007) Ctcf Interacts with and Recruits the Largest Subunit of Rna Polymerase Ii to Ctcf Target Sites Genome-Wide. Molecular and cellular biology.
15. Thorvaldsen J L, Duran K L, Bartolomei M S (1998) Deletion of the H19 differentially methylated domain results in loss of imprinted expression of H19 and Igf2. Genes & development 12: 3693-3702. PMID: 9851976
16. Schoenherr C J. Levorse J M, Tilghman S M (2003) CTCF maintains differential methylation at the Igf2/H19 locus. Nature genetics 33: 66-69. PMID: 12461525
17. Fiorentino F P, Giordano A (2011) The tumor suppressor role of CTCF. J Cell Physiol. doi: 10.1002/jcp. 22780
18. Kurukuti S, Tiwari V K, Tavoosidana G, Pugacheva E, Murrell A. et al. (2006) CTCF binding at the H19 imprinting control region mediates maternally inherited higher-order chromatin conformation to restrict enhancer access to Igf2. Proceedings of the National Academy of Sciences of the United States of America 103: 10684-10689. PMID:
19. Grunau C. Clark S J, Rosenthal A (2001) Bisutfite genomic sequencing: systematic investigation of critical experimental parameters. Nucleic Acids Research 29: e65-e65. doi: 10.1093/nar/29.13.e65 PMID: 11433041
20. Dupont J-M. Tost J, Jammes H, Gut I G (2004) De novo quantitative bisulfite sequencing using the pyrosequencing technology. Analytical Biochemistry 333: 119-127. doi: 10.1016/j.ab.2004.05.007 PMID: 15351288
21. Tost J, Jammes H, Dupont J M, Buffat C, Robert B. et al. (2006) Non-random, individual-specific methylation profiles are present at the sixth CTCF binding site in the human H19/IGF2 imprinting control region. Nucleic Acids Research 34: 5438-5448. PMID: 17012269
22. Klenova E M. Morse H C, Ohlsson R, Lobanenkov W (2002) The novel BORIS+CTCF gene family is uniquely involved in the epigenetics of normal biology and cancer. Seminars in cancer biology 12: 399-414. PMID: 12191639
23. Loukinov D I, Pugacheva E, Vatolin S, Pack S D, Moon H, et al. (2002) BORIS, a novel male germ-linespecific protein associated with epigenetic reprogramming events, shares the same 11-zinc-finger domain with CTCF, the insulator protein involved in reading imprinting marks in the soma. Proceedings of the National Academy of Sciences of the United States of America 99: 6806-6811. PMID: 12011441
24. Loukinov D, Ghochikyan A, Mkrtichyan M, Ichim T E, Lobanenkov W, et al. (2006) Antitumor efficacy of DNA vaccination to the epigenetically acting tumor promoting transcription factor BORIS and CD80 molecular adjuvant. J Cell Blochem 98: 1037-1043. doi: 10.1002/jcb.20953 PMID: 16741971
25. Jones T A. Ogunkolade B W, Szary J, Aarum J, Mumin M A, et al. (2011) Widespread expression of BORIS/CTCFL in normal and cancer cells. PLoS ONE 6: e22399. doi: 10.1371/joumal.pone.0022399 PMID: 21811597
26. Woloszynska-Read A, Zhang W, Yu J, Link P A, Mhawech-Fauceglia P. et al. (2011) Coordinated cancer germline antigen promoter and global DNA hypomethylation in ovarian cancer: association with the BORIS/CTCF expression ratio and advanced stage. Clin Cancer Res 17: 2170-2180. doi: 10.1158/1078-0432.CCR-10-2315 PMID: 21296871
27. Renaud S, Pugacheva E M, Delgado M D, Braunschweig R, Abdullaev Z, et al. (2007) Expression of the CTCF-paralogous cancer-testis gene, brother of the regulator of imprinted sites (BORIS), is regulated by three alternative promoters modulated by CpG methylation and by CTCF and p53 transcription factors. Nucleic Acids Research 35: 7372-7388. PMID: 17962299
28. Burke L J. Zhang R, Bartkuhn M. Tiwari V K, Tavoosidana G, et al. (2005) CTCF binding and higher order chromatin structure of the H19 locus are maintained in mitotic chromatin. The EMBO journal 24: 3291-3300. PMID: 16107875
29. Filippova G N, Qi C F, Ulmer J E, Moore J M, Ward M D, et al. (2002) Tumor-associated zinc finger mutations in the CTCF transcription factor selectively alter tts DNA-binding specificity. Cancer Research 62: 48-52. PMID: 11782357
30. Zhang Y, Shields T, Crenshaw T, Hao Y, Moulton T, et al. (1993) Imprinting of human H19: allele-specific CpG methylation, loss of the active allele in Wilms tumor, and potential for somatic allele switching. American journal of human genetics 53: 113-124. PMID: 8391213
31. Bell A C, Felsenfeld G (2000) Methylation of a CTCF-dependent boundary controls imprinted expression of the Igf2 gene. Nature 405: 482-485. PMID: 10839546
32. Kanduri C, Pant V, Loukinov D, Pugacheva E, Qi C F, et al. (2000) Functional association of CTCF with the insulator upstream of the H19 gene is parent of origin-specific and methylation-sensitive. Curr Biol 10: 853-856. PMID: 10899010
33. Feinberg A P, Cui H. Ohisson R (2002) DNA methylation and genomic imprinting: insights from cancer into epigenetic mechanisms. Seminars in cancer biology 12: 389-398. PMID; Ser. No. 12/191,638
34. Bell A C, West A G, Felsenfeld G (1999) The protein CTCF is required for the enhancer blocking activity of vertebrate insulators. Cell 98: 387-396. PMID: 10458613
35. Wolffe A P (2000) Transcriptional control: imprinting insulation. Curr Biol 10: R463-R465. PMID: 10873799
36. Ulaner G A, Vu T H, Li T, Hu J F, Yao X M, at al. (2003) Loss of imprinting of IGF2 and H19 In osteosarcoma is accompanied by reciprocal methylation changes of a CTCF-binding site. Human molecular genetics 12: 535-549. PMID: 12588801
37. Pant V, Kurukuti S, Pugacheva E, Shamsuddin S, Mariano P, et al. (2004) Mutation of a single CTCF target site within the H19 imprinting control region leads to loss of Igf2 imprinting and complex patterns of de novo methylation upon maternal inheritance. Molecular and cellular biology 24: 3497-3504.PMID: 15060168
38. Jelinic P, Stehle J C, Shaw P (2006) The testis-specific factor CTCFL cooperates with the protein methyltransferase PRMT7 in H19 imprinting control region methylation. PLoS biology 4: e355. PMID: 17048991
39. Adkins R M, Somes G, Morrison J C, Hill J B, Watson E M, et al. (2010) Association of birth weight with polymorphisms in the IGF2. H19, and IGF2R genes. Pediatr Res 68: 429-434. doi: 10.1203/PDR.0b013e3181f1ca99 PMID: 20639793
40. Pearce C L, Doherty J A, Van Den Berg D J, Moysich K. Hsu C, et al. (2011) Genetic variation in insulinlike growth factor 2 may play a role in ovarian cancer risk. Human molecular genetics 20: 2263-2272. doi: 10.1093/hmg/ddr087 PMID: 21422097

41. Neuhausen S L, Brummel S. Ding Y C, Steele L, Nathanson K L, et al. (2011) Genetic Variation in IGF2 and HTRAI and Breast Cancer Risk among BRCA1 and BRCA2 Carriers. Cancer Epidemiology Biomarkers & Prevention 20: 1690-1702. doi: 10.1158/1055-9965.EPI-10-1336 PMID: 21708937
42. Coolen M W, Statham A L, Qu W, Campbell M J, Henders A K, et al. (2011) Impact of the genome on the epigenome is manifested in DNA methylation patterns of imprinted regions in monozygotic and dizygotic twins. PLoS ONE 6: e25590. doi: 10.1371/journal.pone.0025590 PMID: 21991322
43. Sleutels F, Soochit W, Bartkuhn M, Heath H, Dienstbach S, et al. (2012) The male germ cell gene regulator CTCFL is functionally different from CTCF and binds CTCF-like consensus sites in a nucleosome composition-dependent manner. Epigenetics Chromatin 5: 8. doi: 10.1186/1756-8935-5-8 PMID: 22709888 wherein:
  i) the detected genotype of the rs10732516 polymorphism is TT, the patient is classified as a highest risk patient, and the tumor is treated by surgical excision; or
  ii) the detected genotype of the of the rs10732516 polymorphism is TC, where the C allele is determined to be the maternal allele, the patient is classified as a high risk patient, and the tumor is treated by surgical excision.

2. The method of claim 1, wherein determining which allele is the maternal allele and which allele is the paternal allele in a heterozygous genotype at rs10732516, with one thymine allele and one cytosine allele, comprises determining whether the cytosine is methylated;
  whereby:
  when the cytosine is not methylated the C allele is determined to be a maternal allele; and

What is claimed is:

1. A method of risk stratification and treatment of a tumor that expresses Boris in a patient, the method comprising:
  a) detecting the genotype of the rs10732516 thymine/cytosine single nucleotide polymorphism in a sample from the patient; and
  b) if the patient is heterozygous at rs10732516, with one thymine allele and one cytosine allele, determining which allele is the maternal allele and which allele is the paternal allele;

when the cytosine is methylated the C allele is determined to be a paternal allele.

3. The method of claim 2, wherein determining whether the cytosine is methylated comprises spectroscopy of the patient's DNA.

4. The method of claim 2, wherein determining whether the cytosine is methylated comprises bisulfite conversion and quantitative methylation sensitive pyrosequencing.

5. The method of claim 2, wherein determining whether the cytosine is methylated comprises directly sequencing parental DNA.

6. A method of risk stratification and treatment of an infantile hemangioma tumor that expresses Boris in a patient, the method comprising:
   a) detecting the genotype of the rs10732516 thymine/cytosine single nucleotide polymorphism in a sample from the patient; and
   b) if the patient is heterozygous at rs10732516, with one thymine allele and one cytosine allele, determining which allele is the maternal allele and which allele is the paternal allele;
   wherein:
      i) the detected genotype of the rs10732516 polymorphism is TT, the patient is classified as a highest risk patient, and the tumor is treated by surgical excision or chemotherapy; or
      ii) the detected genotype of the of the rs10732516 polymorphism is TC, where the C allele is determined to be the maternal allele, the patient is classified as a high risk patient, and the tumor is treated by surgical excision or chemotherapy.

7. The method of claim 1 wherein the tumor is breast cancer.

8. The method of claim 1 wherein the tumor is ovarian cancer.

9. The method of claim 1 wherein the tumor is testicular cancer.

10. The method of claim 1 wherein the tumor is liver cancer.

11. The method of claim 1 wherein the tumor is lung cancer.

12. The method of claim 1 wherein the tumor is brain cancer.

* * * * *